(12) United States Patent
Zambrowicz et al.

(10) Patent No.: US 6,436,707 B1
(45) Date of Patent: *Aug. 20, 2002

(54) VECTORS FOR GENE MUTAGENESIS AND GENE DISCOVERY

(75) Inventors: Brian Zambrowicz; Glenn A. Friedrich, both of The Woodlands; Stan Lilleberg, Spring; Arthur T. Sands, The Woodlands, all of TX (US)

(73) Assignee: Lexicon Genetics Incorporated, The Woodlands, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/276,533

(22) Filed: Mar. 25, 1999

Related U.S. Application Data

(60) Provisional application No. 60/079,729, filed on Mar. 27, 1998, provisional application No. 60/081,727, filed on Apr. 14, 1998, and provisional application No. 60/109,302, filed on Nov. 20, 1998.

(51) Int. Cl.⁷ .......................... C12N 15/00; C12N 15/63; C12N 15/86; A01N 63/00; C07H 21/02
(52) U.S. Cl. .................... 435/455; 435/320.1; 435/325; 435/456; 424/93.21; 536/23.1
(58) Field of Search ................................ 435/320.1, 325, 435/455, 456, 463; 800/8, 13; 424/93.21; 536/23.1

(56) References Cited

U.S. PATENT DOCUMENTS

| | | |
|---|---|---|
| 4,190,496 A | 2/1980 | Rubenstein et al. |
| 4,959,317 A | 9/1990 | Sauer |
| 5,449,614 A | 9/1995 | Danos et al. |
| 5,464,764 A | 11/1995 | Capecchi et al. |
| 5,521,076 A | 5/1996 | Mulligan et al. |
| 5,523,226 A | 6/1996 | Wheeler |
| 5,625,048 A | 4/1997 | Tsien et al. |
| 5,654,182 A | 8/1997 | Wahl et al. |
| 5,656,479 A | 8/1997 | Petitte et al. |
| 5,679,523 A | 10/1997 | Li et al. |
| 5,690,926 A | 11/1997 | Hogan |
| 5,733,761 A | 3/1998 | Treco et al. |
| 5,767,336 A | 6/1998 | Skarnes |
| 5,789,653 A | 8/1998 | Skarnes |
| 6,080,576 A * | 6/2000 | Zambrowicz et al. ..... 435/320.1 |

FOREIGN PATENT DOCUMENTS

| | | |
|---|---|---|
| WO | WO 94/24301 * | 10/1994 |
| WO | WO 97/02323 | 1/1997 |
| WO | WO 97/06816 | 2/1997 |
| WO | WO 98/20031 | 5/1998 |

OTHER PUBLICATIONS

Campbell et al., 1997, "Totipotency or Multipotentially of Cultured Cells: Applications and Progress", Phenogenology 47:63–72.

Chang et al., 1993, "Enrichment of insertional mutants following retrovirus gene trap selection", Virology 193(2):737–747.

Cho et al., "Revertants of Human Cells Transformed by Murine Sarcoma Virus", Science, 194:951–953.

Deng et al., 1995, "An insertional mutation in the BTF3 transcription factor gene leads to an early postimplantation lethality in mice", Transgenic Res. 4(4):264–269.

Evans et al., 1997, "Gene trapping and functional genomics", Trends in Genetics 13(9):370–374.

Forrester et al., 1996, "An induction gene trap screen in embryonic stem cells: identification of genes that respond to retinoic acid in vitro", Proc. Natl. Acad. Sci. USA 93:1677–1682.

Frohman, 1994, "On Beyond Classic RACE (Rapid Amplification of cDNA Ends)", PCR Methods and Applications, 4:S40–S58.

Gasca et al., 1995, "Characterization of a gene trap insertion into a novel gene, cordon–bleu, expressed in axial structures of the gastrulating mouse embyro", Dev. Genet. 17:141–154.

Gogos et al., 1996, "Gene trapping in differentiating cell lines: regulation of the lysosomal protease cathepsin B in skeletal myoblast growth and fusion", J. Cell Biol. 134(4):837–847.

Gogos et al., 1997, "Selection for retroviral insertions into regulated genes", J. Virol. 71(2):1644–1650.

Hicks et al., 1997, "Functional genomics in mice by tagged sequence mutagenesis", Nature Genetics 16(4):338–344.

Hotfilder et al., 1994, "Isolation of developmentally–Regulated genes from a hemotapoietic progenitor–cell line using a retroviral gene–trap–vector", J. Cellular Biochemistry S18A:11.

Inoue et al., 1983, "Rat Mutant Cells Showing Temperature Sensitivity for Transformation by Wild–Type Moloney Murine Sarcoma Virus", Virology, 125:242–245.

Jonsson et al., 1996, "Use of a promoter–trap retrovirus to identify and isolate genes involved in differentiation of a myeloid progenitor cell line in vitro", Blood 87(5):1771–1779.

(List continued on next page.)

Primary Examiner—Scott D. Priebe
Assistant Examiner—Shin-Lin Chen
(74) Attorney, Agent, or Firm—Finnegan, Henderson, Farabow, Garrett & Dunner, L.L.P.

(57) ABSTRACT

Novel vectors are described that incorporate, inter alia, a novel 3' gene trap cassette which can be used to efficiently trap and identify previously unknown cellular genes. Vectors incorporating the described 3' gene trap cassette find particular application in gene discovery and in the production of mutated cells and animals.

15 Claims, 3 Drawing Sheets

OTHER PUBLICATIONS

Kang et al., 1997, "Dicistronic tagging of genes active in embyronic stem cells of mice", Mol. Cells 7(4):502–508.

Maruyama et al., 1981, "Characterization of Flat Revertant Cells Isolated from Simian Virus 40–Transformed Mouse and Rat Cells Which Contain Multiple Copies of Viral Genomes", J. Virol., 37:1028–1043.

Mathey–Prevot et al., 1984, "Revertants and Partial Transformants of Rat Fibroblasts Infected with Fujinami Sarcoma Virus", J. Virol., 50(2):325–334.

Natarajan et al., 1995, "A lacZ–hygromycin fusion gene and its use in a gene trap vector for marking embryonic stem cells", Nucleic Acids Res. 23(19):4003–4004.

Niwa et al., 1993, "An efficient gene–trap method using poly A trap vectors and characterization of gene–trap events", J. Biochem. 113(3):343–349.

Norton et al., 1984, "Expression of Kirsten Murine Sarcoma Virus in Transformed Nonproducer and Revertant NIH/3T3 Cells: Evidence for Cell–Mediated Resistance to a Viral Oncogene in Phenotypic Reversion", J. Virol., 50(2):439–444.

Ory et al., 1996, "A stable human–derived packaging cell line for production of high titer retrovirus/vesicular stomatitis virus G pseudotypes", Proc. Natl. Acad. Sci. USA, 93:11400–11406.

Pestov and Lau, 1994, "Genetic selection of growth–inhibitory sequences in mammalian cells", Proc. Natl. Acad. Sci. USA, 91:12549–12553.

Ryan et al., 1985, "Isolation of a Simian Virus 40 T–Antigen–Positive, Transformation–Resistant Cell Line by Indirect Selection", Mol. Cell. Biol., 5(12):3577–3582.

Sablitzky et al., 1990, "Isolation of developmentally regulated genes expressed by hematopoietic stem cells using a retroviral enhancer trap vector", J. Cell Biochem. Suppl., Symposia on Molecular and Cellular Biology, Park City, Utah, Mar. 31–Apr. 6, 209 (M132).

Sacks et al., 1979, "Abelson Murine Leukemia Virus–Infected Cell Lines Defective in Transformation", Virology, 97:231–240.

Selten et al., 1985, "Proviral activation of the putative oncogene Pim–1 in MuLV induced T–cell lymphomas", EMBO J., 4(7):1793–1798.

Shirai et al., 1996, "A gene trap strategy for identifying the gene expressed in the embyronic nervous system", Zoolog. Sci. 13(2):277–283.

Skarnes, 1993, "The identification of new genes: gene trapping in transgenic mice", Current Opinion in Biotechnology 4:684–689.

Skarnes et al., 1992, "A gene trap approach in mouse embryonic stem cells: the lacZ reporter is activated by splicing, relfects endogenous gene expression, and is mutagenic in mice", Genes Dev. 6(6):903–918.

Songyang et al., 1993, "SH2 Domains Recognize Specific Phosphopeptide Sequences", Cell 72:767–778.

Steinberg et al., 1978, "Isolation and characterization of T Antigen–negative revertants from a line of transformed rat cells containing one copy of the SV40 Genome", Cell, 13:19–32.

Stephenson et al., 1973, "Characterization of Morphologic Revertants of Murine and Avian Sarcoma Virus–Transformed Cells", J. Virol., 11(2):218–222.

Varmus et al., 1981, "Retroviruses as Mutagens: Insertion and Excision of a Nontransforming Provirus Alter Expression of a Resident Transforming Provirus", Cell, 25:23–36.

Varmus et al., 1981, "Revertants of an ASV–Transformed Rat Cell Line Have Lost the Complete Provirus or Sustained Mutations in src", Virology, 108:28–46.

Vitaterna et al., 1994, "Mutagenesis and Mapping of a Mouse Gene, Clock, Essential for Circadian Behavior", Science, 264:719–725.

Wilson et al., 1986, "A Frameshift at a Mutational Hotspot in the Polyoma Virus Early Region Generates Two New Proteins that Define T–Antigen Functional Domains", Cell, 44:477–487.

Wurst et al., 1995, "A large–scale gene–trap screen for insertional mutations in developmentally regulated genes in mice", Genetics, 139:889–899.

Zambrowicz et al., 1997, "Disruption of overlapping transcripts in the ROSA beta geo 26 gene trap strain leads to widespread expression of beta–galactosidase in mouse embyros and hematopoietic cells", Proc. Natl. Acad. Sci. USA 94(8):3789–3794.

Patriotis et al., "The activated Mlvi–4 locus in Moloney murine leukemia virus–induced rat T–cell lymphomas encodes an Env/Mlvi–4 fusion protein", J. Virol., 68(12):7927–7932, Dec. 1994.*

Duyk et al., "Exon trapping: a genetic screen to identify candidate transcribed sequences in cloned mammalian genomic DNA", Proc. Natl. Acad. Sci USA, 87:8995–8999, Nov. 1990.*

Yoshida et al., "A new strategy of gene trapping in ES cells using 3'Race", Transgenic Res., 4(4):277–287, Jul. 1995.*

Skarnes, "The identification of new genes: gene trapping in transgenic mice", Curr. Opin. Biotechnol., 4(6):684–689, 1993.*

* cited by examiner

5'CACGTCTGCAGTCCGGAGGAGTGTGTTTCTCCTCCGCTGATGAGTCCG
TGAGGACGAAACTGCAGACGTG3'

Predicted secondary structure and cleavage site for LEX-SCS2 transcribed RNA

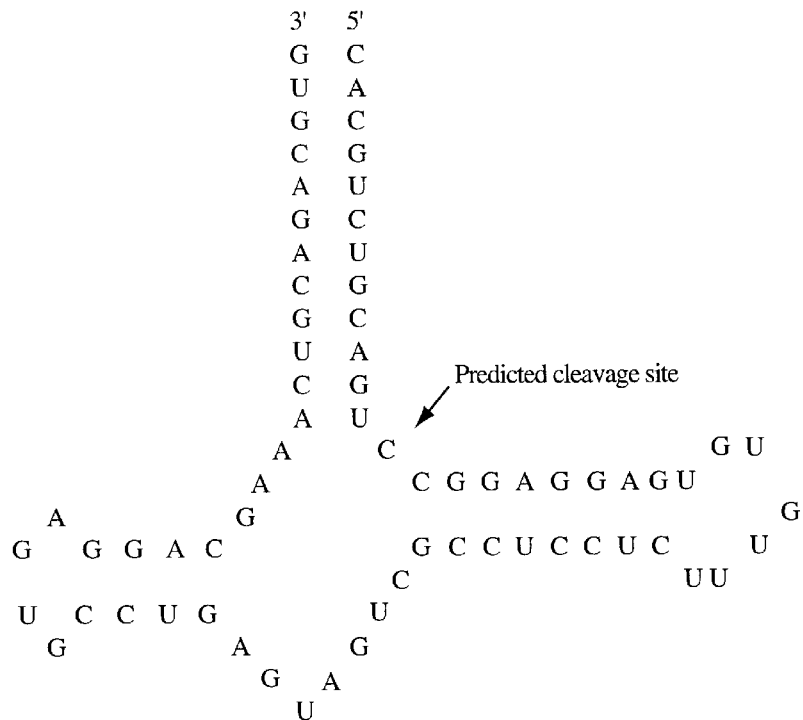

FIG. 3b

GGATCCGAATTCTCGAGGCTAAGCCAGTTTTCGTACCCTTGACTGCGTTTCAT
CGATTCGCTACTAACATTGCCTTTTCCTCCTTCCCTCCCACAGGTGGAAGAGC
TCGGGTACCAGGAGAGGAGAGGAGAGGAGAGGAGAGGAGAGGAGAGGAG
AGGAGAGGAGAGGAGAGGAGATCTCAGGTGAGTTCGCATGTGCTTCGAACT
TGTGTGCATGCGTTCTAAAAGGGCTTCTCTTGGTGTTCGATCTGGGGCTAAGC
TTAATTAAGAATTCGGATCC

FIG. 4

SEQUENCE LISTING

```
<160> NUMBER OF SEQ ID NOS: 24

<210> SEQ ID NO 1
<211> LENGTH: 68
<212> TYPE: DNA
<213> ORGANISM: Artificial Sequence
<220> FEATURE:
<223> OTHER INFORMATION: Synthetic sequence

<400> SEQUENCE: 1
cacgtctgca gatcatgagg atgctaatcc ttgatggcat gcactatgcg cgatgatctg     60
cagacgtg                                                              68

<210> SEQ ID NO 2
<211> LENGTH: 68
<212> TYPE: RNA
<213> ORGANISM: Artificial Sequence
<220> FEATURE:
<223> OTHER INFORMATION: Synthetic sequence

<400> SEQUENCE: 2
cacgucugca gaucaugagg augcuaaucc uugauggcau gcacuaugcg cgaugaucug     60
cagacgug                                                              68

<210> SEQ ID NO 3
<211> LENGTH: 70
<212> TYPE: DNA
<213> ORGANISM: Artificial Sequence
<220> FEATURE:
<223> OTHER INFORMATION: Synthetic sequence

<400> SEQUENCE: 3
cacgtctgca gtccggagga gtgtgtttct cctccgctga tgagtccgtg aggacgaaac     60
tgcagacgtg                                                            70

<210> SEQ ID NO 4
<211> LENGTH: 70
<212> TYPE: RNA
```

<213> ORGANISM: Artificial Sequence
<220> FEATURE:
<223> OTHER INFORMATION: Synthetic sequence

<400> SEQUENCE: 4

```
cacgucugca guccggagga guguguuucu ccuccgcuga ugaguccgug aggacgaaac    60
ugcagacgug                                                          70
```

<210> SEQ ID NO 5
<211> LENGTH: 279
<212> TYPE: DNA
<213> ORGANISM: Artificial Sequence
<220> FEATURE:
<223> OTHER INFORMATION: Synthetic sequence

<400> SEQUENCE: 5

```
ggatccgaat tctcgaggct aagccagttt tcgtacccct tgactgcgttt catcgattcg    60
ctactaacat tgcctttttcc tccttccctc ccacaggtgg aagagctcgg gtaccaggag  120
aggagaggag aggagaggag aggagaggag aggagaggag aggagaggag aggagatctc  180
aggtgagttc gcatgtgctt cgaacttgtg tgcatgcgtt ctaaaagggc ttctcttggt  240
gttcgatctg gggctaagct taattaagaa ttcggatcc                          279
```

<210> SEQ ID NO 6
<211> LENGTH: 43
<212> TYPE: DNA
<213> ORGANISM: Mus musculus

<400> SEQUENCE: 6

```
gcaaccagta acctctgccc tttctcctcc atgacaacca ggt                     43
```

<210> SEQ ID NO 7
<211> LENGTH: 41
<212> TYPE: DNA
<213> ORGANISM: Adenovirus

<400> SEQUENCE: 7

```
gatgatgtca tacttatcct gtccctttttt tttccacagc t                      41
```

<210> SEQ ID NO 8
<211> LENGTH: 35
<212> TYPE: DNA
<213> ORGANISM: Mus musculus

<400> SEQUENCE: 8

```
ggcggtcagg ctgccctctg ttcccattgc aggaa                              35
```

<210> SEQ ID NO 9
<211> LENGTH: 42
<212> TYPE: DNA
<213> ORGANISM: Mus musculus

<400> SEQUENCE: 9

```
tgtcagtctg tcatccttgc cccttcagcc gcccggatgg cg                      42
```

<210> SEQ ID NO 10
<211> LENGTH: 39
<212> TYPE: DNA
<213> ORGANISM: Mus musculus

<400> SEQUENCE: 10

```
tgctgacacc ccactgttcc ctgcaggacc gccttcaac                          39
```

<210> SEQ ID NO 11
<211> LENGTH: 34
<212> TYPE: DNA
<213> ORGANISM: Mus musculus

<400> SEQUENCE: 11
taattgtgta attattgttt ttcctccttt agat                          34

<210> SEQ ID NO 12
<211> LENGTH: 40
<212> TYPE: DNA
<213> ORGANISM: Mus musculus

<400> SEQUENCE: 12
cagaatcttc tttttaattc ctgattttat ttctatagga                    40

<210> SEQ ID NO 13
<211> LENGTH: 37
<212> TYPE: DNA
<213> ORGANISM: Artificial Sequence
<220> FEATURE:
<223> OTHER INFORMATION: Synthetic sequence

<400> SEQUENCE: 13
tactaacatt gcctttcct ccttccctcc cacaggt                        37

<210> SEQ ID NO 14
<211> LENGTH: 37
<212> TYPE: DNA
<213> ORGANISM: Mus musculus

<400> SEQUENCE: 14
tgctccactt tgaaacagct gtctttcttt tgcagat                       37

<210> SEQ ID NO 15
<211> LENGTH: 36
<212> TYPE: DNA
<213> ORGANISM: Mus musculus

<400> SEQUENCE: 15
ctctctgcct attggtctat tttcccaccc ttaggc                        36

<210> SEQ ID NO 16
<211> LENGTH: 35
<212> TYPE: DNA
<213> ORGANISM: Mus musculus

<400> SEQUENCE: 16
attaattact ctgcccattc ctctctttca gagtt                         35

<210> SEQ ID NO 17
<211> LENGTH: 52
<212> TYPE: DNA
<213> ORGANISM: Artificial Sequence
<220> FEATURE:
<223> OTHER INFORMATION: Primer

<400> SEQUENCE: 17
ccagtgagca gagtgacgag gactcgagct caagcttttt tttttttttt tt      52

<210> SEQ ID NO 18
<211> LENGTH: 23
<212> TYPE: DNA

<213> ORGANISM: Artificial Sequence
<220> FEATURE:
<223> OTHER INFORMATION: Primer

<400> SEQUENCE: 18
aagcccggtg cctgactagc tag         23

<210> SEQ ID NO 19
<211> LENGTH: 22
<212> TYPE: DNA
<213> ORGANISM: Artificial Sequence
<220> FEATURE:
<223> OTHER INFORMATION: Primer

<400> SEQUENCE: 19
gaatatgtct ccaggtccag ag          22

<210> SEQ ID NO 20
<211> LENGTH: 23
<212> TYPE: DNA
<213> ORGANISM: Artificial Sequence
<220> FEATURE:
<223> OTHER INFORMATION: Primer

<400> SEQUENCE: 20
ccagtgagca gagtgacgag gac         23

<210> SEQ ID NO 21
<211> LENGTH: 18
<212> TYPE: DNA
<213> ORGANISM: Artificial Sequence
<220> FEATURE:
<223> OTHER INFORMATION: Primer

<400> SEQUENCE: 21
ctagctaggg agctcgtc               18

<210> SEQ ID NO 22
<211> LENGTH: 23
<212> TYPE: DNA
<213> ORGANISM: Artificial Sequence
<220> FEATURE:
<223> OTHER INFORMATION: Primer

<400> SEQUENCE: 22
ccagagtctt cagagatcaa gtc         23

<210> SEQ ID NO 23
<211> LENGTH: 18
<212> TYPE: DNA
<213> ORGANISM: Artificial Sequence
<220> FEATURE:
<223> OTHER INFORMATION: Primer

<400> SEQUENCE: 23
gaggactcga gctcaagc               18

<210> SEQ ID NO 24
<211> LENGTH: 20
<212> TYPE: DNA

-continued

```
<213> ORGANISM: Artificial Sequence
<220> FEATURE:
<223> OTHER INFORMATION: Primer

<400> SEQUENCE: 24
ctgtaaaacg acggccagtc                                               20
```

VECTORS FOR GENE MUTAGENESIS AND GENE DISCOVERY

The present application claims priority to U.S. provisional application Ser. No. 60/079,729, file Mar. 27, 1998, No. 60/081,727, filed Apr. 14, 1998 and No. 60/109,302 filed Nov. 20, 1998, which are herein incorporated by reference in their entirety.

1.0. FIELD OF THE INVENTION

The present invention relates to recombinant vectors incorporating structural elements that, after the vectors have integrated into the host cell genome, enhance the number of cellular genes that can be identified as well as effectively mutated. The described vectors are important tools for both gene discovery, gene cloning, gene mutation, gene regulation, shuttling nucleic acid sequences throughout the genome, and gene activation and over expression.

2.0. BACKGROUND OF THE INVENTION

Gene trapping provides a powerful approach for simultaneously mutating and identifying genes. Gene trap vectors can be nonspecifically inserted into the target cell genome, and gene trap vectors have consequently been constructed that select for events in which the gene trap vector has inserted into and mutated a gene. By exploiting the cellular splicing machinery, the selectable nature of these vectors removes the large background of insertion events where vectors have not integrated into genes.

Most mammalian genes are divided into exons and introns. Exons are the portions of the gene that are spliced into mRNA and encode the protein product of a gene. In genomic DNA, these coding exons are divided by noncoding intron sequences. Although RNA polymerase transcribes both intron and exon sequences, the intron sequences must be removed from the transcript so that the resulting mRNA can be translated into protein. Accordingly, all mammalian, and most eukaryotic, cells have the machinery to splice exons into mRNA. Gene trap vectors have been designed to integrate into introns or genes in a manner that allows the cellular splicing machinery to splice vector encoded exons to cellular mRNAs. Often, such gene trap vectors contain selectable marker sequences that are preceded by strong splice acceptor sequences and are not preceded by a promoter. Accordingly, when such vectors integrate into a gene, the cellular splicing machinery splices exons from the trapped gene onto the 5' end of the selectable marker sequence. Typically, such selectable marker genes can only be expressed if the vector encoding the gene has integrated into an intron. The resulting gene trap events are subsequently identified by selecting for cells that can survive selective culture.

Gene trapping has proven to be a very efficient method of mutating large numbers of genes. The insertion of the gene trap vector creates a mutation in the trapped gene, and also provides a molecular tag that can be exploited to identify the trapped gene. When ROSAβgeo was used to trap genes it was demonstrated that at least 50% of the resulting mutations resulted in a phenotype when examined in mice. This indicates that the gene trap insertion vectors are useful mutagens. Although a powerful tool for mutating genes, the potential of the method had been limited by the difficulty in identifying the trapped genes. Methods that have been used to identify trap events rely on the fusion transcripts resulting from the splicing of exon sequences from the trapped gene to sequences encoded by the gene trap vector. Common gene identification protocols used to obtain sequences from these fusion transcripts include 5' RACE, cDNA cloning, and cloning of genomic DNA surrounding the site of vector integration. However, these methods have proven labor intensive, not readily amenable to automation, and generally impractical for high-throughput.

3.0. SUMMARY OF THE INVENTION

Recently, vectors have been developed that rely on a new strategy of gene trapping that uses a vector that contains a selectable marker gene preceded by a promoter and followed by a splice donor sequence instead of a polyadenylation sequence. These vectors do not provide selection unless they integrate into a gene and subsequently trap downstream exons that provide the polyadenylation sequence required for expression of the selectable marker. Integration of such vectors into the chromosome results in the splicing of the selectable marker gene to 3' exons of the trapped gene. These vectors provide a number of advantages. They can be used to trap genes regardless of whether the genes are normally expressed in the cell type in which the vector has integrated. In addition, cells harboring such vectors can be screened using automated (e.g., 96-well plate format) gene identification assays such as 3' RACE (see generally, Frohman, 1994, PCR Methods and Applications, 4:S40–S58). Using these vectors it is possible to produce large numbers of mutations and rapidly identify the mutated, or trapped, gene. However, prior to the present invention, the commercial scale exploitation of such vectors has been limited by the number of target genes that can be efficiently trapped using such vectors.

The relative inefficiency of first generation 3' gene trap vectors has limited the total number of genes that can be rapidly and practically trapped, identified, analyzed, and effectively mutated. This inefficiency prompted the development of more efficient methods of 3' gene trapping-methods that allow a greater percentage of genes in the target cell genome to be trapped and rapidly identified by, for example, DNA sequence analysis.

The present invention relates to the construction of novel vectors comprising a 3' gene trap cassette that allows for high efficiency 3' gene trapping. The presently described 3' gene trap cassette comprises in operable combination, a promoter region, an exon (typically characterized by a translation initiation codon and open reading frame and/or internal ribosome entry site), a splice donor sequence, and, optionally, intronic sequences. The splice donor (SD) sequence is operatively positioned such that the exon of the 3' gene trap cassette is spliced to the splice acceptor (SA) site of a downstream exon or a cellularly encoded exon. As such, the described 3' gene trap cassette (or gene trap vector incorporating the same) shall not incorporate a splice acceptor (SA) sequence and a polyadenylation site operatively positioned downstream from the SD sequence of the gene trap cassette. In a preferred embodiment, the exon component of the 3' gene trap cassette, which also serves as a sequence acquisition cassette, will comprise exon sequence and a splice donor sequence derived from genetic material that naturally occurs in an eukaryotic cell.

An additional embodiment of the present invention is the use of the described vectors to acquire novel DNA sequence information from gene trapped exons from an infected target cell or a plurality of target cells.

Additional embodiments of the present invention include recombinant vectors, particularly viral vectors, that have been genetically engineered to incorporate the described 3' gene trap cassette. Preferably, although not necessarily, these vectors will additionally incorporate a selectable marker that allows for maintenance and detection of vector sequence in the target cell. The selectable marker can be utilized as a 5' gene trap cassette that is placed upstream from, and in the same orientation as, the 3' gene trap cassette. Optionally, a 5' gene trap cassette incorporating a selectable marker can be used in conjunction with a vector encoded mutagenic mini-exon sequence operably positioned, inter alia, to enhance splicing of cellular transcripts to the selectable marker of the 5' gene trap cassette.

Additionally, the vector can include one or more mutagenesis enhancer sequence(s) such as, but not limited to, a sequence encoding a self-cleaving RNA, a transcription terminator, an exon that changes the reading frame (or encodes one or more stop codons), and/or a terminal exon, or any mixture or combination thereof, operatively positioned between the 5' gene trap cassette and the 3' gene trap cassette of the disclosed vectors.

An additional embodiment of the present invention is the use of the novel 3' gene trap cassette, or vectors comprising the same, to mutate and trap genes in a population of target cells, or tissues, in vitro or in vivo, and/or to obtain the polynucleotide sequence of unknown genes (i.e., discover new genes). As such, general methods of gene mutation, identification, and phenotypic screening are described that use the described 3' gene trap cassette, and vectors comprising the same.

Another embodiment of the present invention is the use of the presently described vectors (e.g., viral vectors comprising a mini-exon and/or 3' gene trap cassette) to activate gene expression in target cells. Preferably, the vectors are retroviral vectors that are nonspecifically integrated (using viral integration machinery) into the target cell genome. Additionally, assays are described that employ the described 3' gene trap cassette, or vectors incorporating the same, to activate, genetically or phenotypically select for, and subsequently identify new genes.

Additional embodiments of the presently described invention include libraries of eukaryotic cells having genes that have been simultaneously mutated (by one or more of the described mutagenic components), and identified (using the described 3' gene trap cassette) using the described vectors, and/or cDNA libraries produced by exploiting the targeting frequency and the sequence acquisition features of the described vectors.

Another embodiment of the present invention is a method of obtaining DNA sequence information from a target cell, comprising the steps of nonspecifically integrating a 3' gene trap cassette (or mutagenic mini-exon), obtaining the chimeric RNA transcript produced when the gene trap cassette (or mutagenic mini-exon) is spliced by the target cell's endogenous splicing machinery to an endogenous exon encoded within the target cell genome, and obtaining sequence information from the endogenously encoded exon from the target cell genome.

4.0. DESCRIPTION OF THE FIGURES

FIG. 1 presents a diagrammatic representation of how the presently described 3' gene trap cassette is spliced to cellular exons after the cassette is incorporated into the target cell genome.

FIG. 2 shows a dual (5' and 3') gene trap vector that incorporates a selectable marker in the 5' trap and the presently described 3' gene trap. FIG. 2 also shows the positions of recombinase recognition, e.g. frt or lox, sites that can be located, for example, 5' to the promoter of the 3' gene trap cassette and 3' to the SD of the 3' gene trap cassette as well as the preferable locations of optional features such as a vector encoded mutagenic mini-exon present upstream from the 5' gene trap cassette, and mutagenesis enhancer cassettes such as a unidirectional transcription termination sequence, a mutagenic terminal exon, and a self-cleaving RNA coding region. The displayed features are in reverse-orientation relative to the flanking LTRs.

FIG. 3b shows the DNA sequence (SEQ ID NO:3) and the RNA sequence (SEQ ID NO:4) of a self-cleaving RNA that can be used as a mutagenesis enhancer.

FIG. 4 shows a representative example of a mutagenic mini-exon sequence (SEQ ID NO:5) that can be used in conjunction with the presently described vectors.

5.0. DETAILED DESCRIPTION OF THE INVENTION

Figure 1:
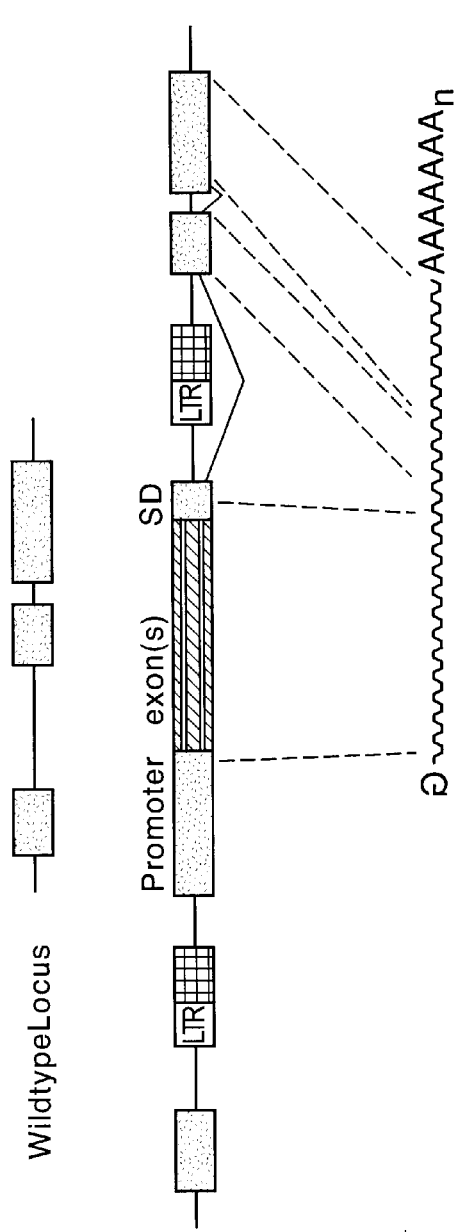

In the modern age of genomics, gene trapping has proven to be a powerful approach for both grouping gene sequences into functional categories, and identifying novel genes. For example, initial results have shown that about half of the gene trap events from embryonic stem cells thus far characterized identify gene sequences that have not been previously discovered by traditional cDNA library technology.

Gene trapping (using promoter traps) has been used in a variety of cell types to genetically screen for genes that are induced by inductive signals, differentiation events, or phenotypes of interest (i.e., in gene discovery). Additionally, such screens have been used to identify tumor suppressor genes, genes induced by cellular differentiation processes such as hematopoietic and muscle cell differentiation, genes induced by signals that induce cellular events such as B cell activation or apoptosis, and genes activated by small molecules or other compounds. These studies indicate that gene trapping can be used to group genes based upon their function in important cellular and physiological processes. However, the broader exploitation of these screens has been limited by the difficulty of identifying the trapped genes.

Several of the issues that must generally be addressed when designing gene trap vectors include, but are not limited to: 1) the percentage of the target cell genome that can be effectively trapped by a given vector ("target size"); 2) the mutagenicity of the vector after insertion into a gene in a target cell; and 3) identifying the mutated gene by sequencing the chimeric transcript produced by gene trap event. The present vectors have been engineered to address the above concerns by, for example, incorporating features that optimize the efficiency of the splice acceptors and splice donors present in the vectors.

5.1. The Broad Applicability of the Described Vectors

The presently described vectors can be used in virtually any type of eukaryotic cell that can be manipulated to insert a gene trap vector into the genome of the cell. For example, vectors that incorporate the presently described 3' gene trap cassette can be used to trap genes and/or acquire sequence information from primary animal tissues as well as any other eukaryotic cell or organism including, but not limited to, yeast, molds, fungi, and plants. Plants of particular interest include dicots and monocots, angiosperms (poppies, roses, camellias, etc.), gymnosperms (pine, etc.), sorghum, grasses, as well as plants of agricultural significance such as, but not limited to, grains (rice, wheat, corn, millet, oats, etc.), nuts, lentils, chick peas, tubers (potatoes, yams, taro, etc.), herbs, cotton, hemp, coffee, cocoa, tobacco, rye, beets, alfalfa, buckwheat, hay, soy beans, bananas, sugar cane, fruits (citrus and otherwise), grapes, vegetables, and fungi (mushrooms, truffles, etc.), palm, maple, redwood, rape seed, safflower, saffron, coconut yew, oak, and other deciduous and evergreen trees. Alternatively, linearized 3' gene trap cassettes can be introduced to target cells using the described conventional methods of nucleotide delivery.

Additional examples of suitable animal target cells include, but are not limited to, mammalian, including human, or avian endothelial cells, epithelial cells, islets, neurons or neural tissue, mesothelial cells, osteocytes, lymphocytes, chondrocytes, hematopoietic cells, immune cells, cells of the major glands or organs (e.g., lung, heart, stomach, pancreas, kidney, skin, etc.), exocrine and/or endocrine cells, embryonic and other totipotent or pluripotent stem cells, fibroblasts, and culture adapted and/or transformed versions of the above can be used in conjunction with the described vectors. Additionally, tumorigenic or other cell lines can be targeted by the presently described vectors.

Preferred target cells for gene trapping using the described vectors are embryonic stem cells (ES cells). ES cells are pluripotent or totipotent. Thus, ES cells that have been genetically engineered in vitro, can subsequently be introduced into a developing fetus or embryo (e.g., into a morula or a blastocyst) to result in chimeric animals. These chimeric animals can subsequently be bred to produce offspring that are heterozygous or homozygous for the engineered allele. In the case of mammalian animals, the ES cells are typically microinjected into blastocysts which are then implanted into pseudopregnant host animals.

The broad applicability of the described ES cell technology is shown in the number of different animal systems to which the technology has been successfully applied. For example, and not by way of limitation, ES cells and/or transgenic animals have been described in avian systems (U.S. Pat. No. 5,656,479), swine (U.S. Pat. No. 5,523,226), non-murine pluripotential cells (U.S. Pat. No. 5,690,926), cattle, sheep, goats, rabbits, and mink (U.S. Application Ser. No. 60/007689 or WO1996US0018988 filed by White et al., and WO1997EP0002323), and human ES Cells (U.S. application Ser. No. 08/699,040, filed by Robl et al., abandoned Jun. 6, 2001) all of which are herein incorporated by reference.

Typically, vectors incorporating the presently described features can be introduced into target cells by any of a wide variety of methods known in the art. Examples of such methods include, but are not limited to, electroporation, viral infection, retrotransposition, transposition, microparticle bombardment, microinjection, lipofection, transfection, as cationic lipid complexes, or as non-packaged/complexed, or "naked," DNA.

The vectors described in the present invention can also be used in conjunction with virtually any type of phenotypic or genetic screening protocols both in vitro and in vivo, and the presently described vectors provide the additional advantage of enabling rapid methods of identifying the DNA sequences of the trapped genes.

The structural features of the vectors of the present invention can be incorporated into any vector backbone so that the resulting construct is capable of integrating into the genome of a eukaryotic cell in a substantially non-specific fashion and preferably in a completely non-specific fashion. A large number of vectors known in the art may be used. Possible vectors include, but are not limited to, plasmids or modified viruses, but the vector system must be compatible with the host cell used. Such vectors include, but are not limited to, bacteriophages such as lambda derivatives, or plasmids such as PBR322 or pUC plasmid derivatives or the Bluescript vector (Stratagene USA, La Jolla, Calif.). The insertion of the DNA fragments corresponding to the features described below into a suitable vector can, for example, be accomplished by ligating the appropriate DNA fragments into the chosen vector that has complementary cohesive termini. However, if the complementary restriction sites of the DNA fragments are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences.

5.2. Structural Features of the Described Vectors 5.2.1. Marker Gene

Vectors contemplated by the present invention can be engineered to contain selectable marker genes that provide for the selection of cells that have incorporated the marker into the cellular genome. In general, such selectable markers enable facile methods of identifying and selecting for eukaryotic cells that incorporate and express the proteins encoded by the selectable markers. Examples of such selection methods include antibiotic, calorimetric, enzymatic, and fluorescent selection of cells that have integrated a gene trap event. One example of such a selectable marker gene is βgeo, but any of a number of other selectable markers can be employed (for example, see U.S. Pat. No. 5,464,764 herein incorporated by reference). An example of a plant selectable marker is hygromycin phosphotransferase.

Accordingly, one embodiment of the present invention contemplates vectors that are engineered to incorporate, and optionally express, a marker gene that facilitates the tracking and identification of target cells that incorporate the presently described 3' gene trap cassette. Such markers include, but are not limited to, antibiotic resistance genes, calorimetric marker genes, enzymes (e.g., β-lactamase), or other marker genes that mediate the direct or indirect expression of, for example, fluorescent marker genes such as the gene encoding green fluorescent protein, and assays for detecting the same, which are described, inter alia, in U.S. Pat. No. 5,625,048, herein incorporated by reference. For the purposes of the present disclosure, the term "directly," when used in a biological or biochemical context, refers to direct causation of a process that does not require intermediate steps, usually caused by one molecule contacting or binding to another molecule (which can be a molecule of the same type or a different type of molecule). For example, molecule A contacts molecule B, which causes molecule B to exert effect X that is part of a biological process. For the purposes of the present invention, the term "indirectly," when used in a biological or biochemical context, refers to indirect causation that requires intermediate steps, usually caused by two or more direct steps. For example, molecule A contacts molecule B to exert effect X which in turn causes effect Y. Also for the purposes of the present invention, the term "gene" shall refer to any and all discrete coding regions of the cell's genome, as well as associated noncoding and regulatory regions, or shall refer to the region encoding a specific and functional protein product or activity. Additionally, the term "operatively positioned" shall refer to the fact that the control elements or genes are present in the proper orientation and spacing to provide the desired or indicated functions of the control elements or genes. Also for the purposes of the present invention, a gene is "expressed" when a control element in the cell mediates the production of functional and/or detectable levels of mRNA encoded by the gene, or a selectable marker inserted therein, that can subsequently be spliced/processed and, where applicable, translated to produce an active product. A gene is not expressed where the relevant control element in the cell is absent, has been inactivated, or does not mediate the production of functional and/or detectable levels of mRNA encoded by the gene, or a selectable marker inserted therein. For the purposes of the present invention, a mRNA is produced at "functional" levels if, upon translation, it produces a protein having the size and activity normally associated with the corresponding locus.

The marker gene can be incorporated into the described vectors as a self-contained expression cassette including, in operable combination, a marker, promoter for expressing the marker, ribosome binding/translation start site, and polyadenylation sequence. Additionally, the marker can be placed in the vector such that it is expressed from a vector promoter, and can optionally be engineered to functionally incorporate an independent ribosome entry site (IRES) that facilitates marker expression.

5.2.2. 5' Gene Trap Cassette

The presently described vectors can be engineered to include a 5' gene trap cassette that typically contains a splice acceptor site located 5' to an exon (which can encode. a selectable marker gene) followed by an operatively positioned polyadenylation sequence. Typically, vectors incorporating 5' gene traps do not contain promoters that express the exon encoded in the 5' gene trap cassette, and do not encode a splice donor sequence operatively positioned 5' to the splice acceptor of the exon of the 5' gene trap cassette. Consequently, after it is integrated into the cellular chromosome the 5' gene trap cassette intercepts the normal splicing of the upstream gene and acts as a terminal exon. The net effect is that the cellular transcript is disrupted and effectively mutagenized by the 5' gene trap cassette. The 5' gene trap cassette can incorporate a marker gene as the exon component, and can thus be used in lieu of or in addition to the marker gene described in Section 5.2.1.

The structural features of the 5' gene trap cassette can also be manipulated to produce gene trap events that are biased as to where the 5' gene trap has integrated into the cellar genome (for purposes of illustration, and not limitation, the following discussion shall assume that the exon of the 5' gene trap cassette encodes a selectable marker). For example, given that no promoter is present, the marker encoded by a 5' gene trap cassette (that has been engineered without an IRES) can typically only be expressed if it has been integrated into an intron 5' from the translation start site of the endogenous gene. Given the absence of an IRES, if the vector incorporating such a 5' gene trap cassette has integrated into an intron that is downstream from the translation start site of the endogenous gene, the marker can only be expressed if it is present in the correct reading frame to produce a fusion protein that provides selectable marker activity. Accordingly, vectors incorporating such 5' gene trap cassettes can selectively increase the probability that the identified gene trapped sequences begin with sequences 5' to the start of translation.

An alternative method of producing a similar effect employs vectors incorporating a nested set of stop codons present in, or otherwise engineered into, the region between the SA of 5' gene trap cassette and the translation initiation codon of the selectable marker, or such stop codons can located between the end of the selectable marker coding region and the polyadenylation sequence. The selectable marker can also be engineered to contain an independent ribosome entry site (IRES) so that the marker will be expressed in a manner largely independent of the location in which the vector has integrated into the target cell genome. Typically, but not necessarily, an IRES is not used in conjunction with a nested set of stop codons as described, supra.

Figure 2:
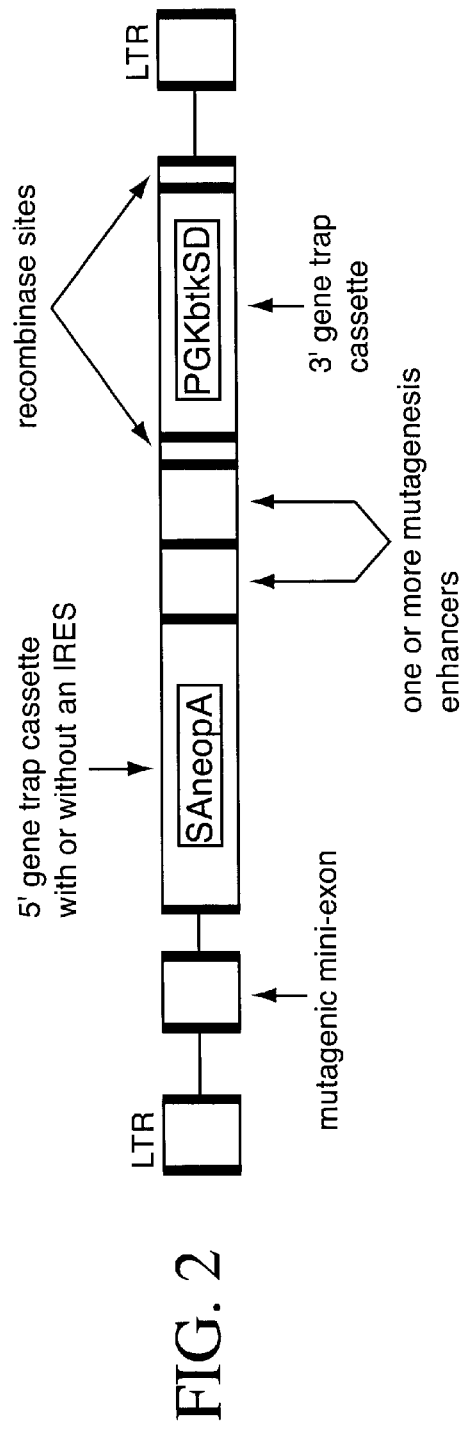
Figure 3A:
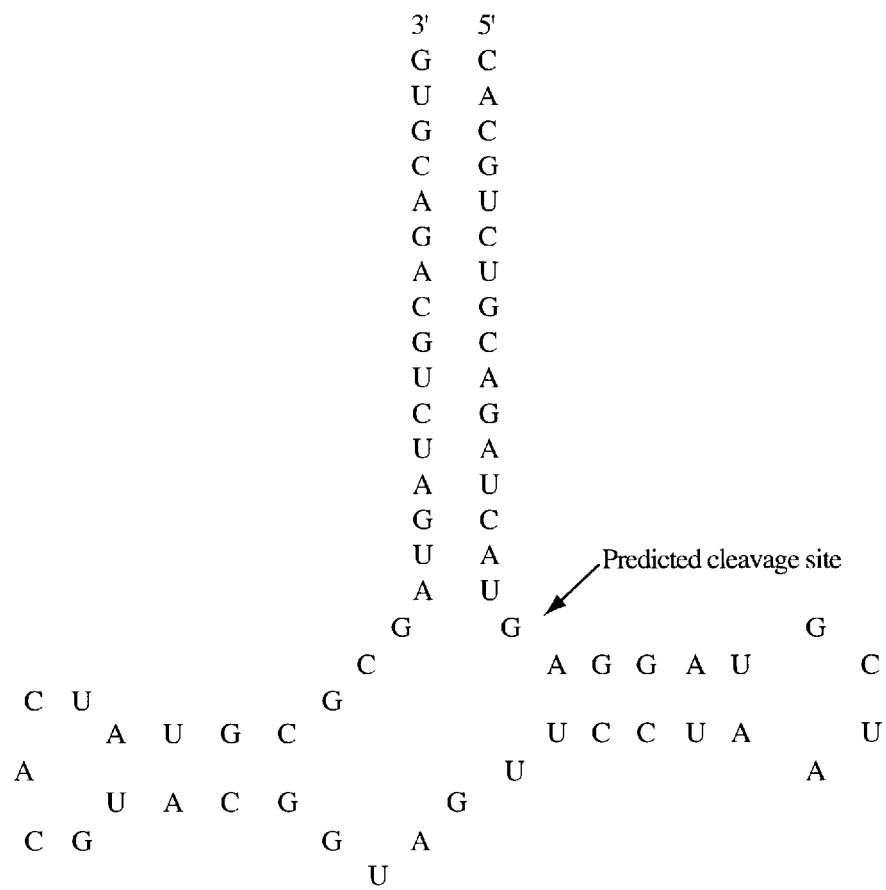
FIG. 3a shows the DNA sequence (SEQ ID NO:1) and the RNA sequence (SEQ ID NO:2) of a self-cleaving RNA that can be used as a mutagenesis enhancer.

In a particularly preferred embodiment, the described vectors employ a 5' gene trap cassette that comprises a selectable marker gene preceded by a splice acceptor sequence and followed a polyadenylation (pA) sequence (SAβgeopA, FIG. 2). Alternatively, SAIRESβgeopA can be used which further incorporates an internal ribosome entry site upstream from the βgeo gene, or SAneopA can be used (which dispenses with the β-gal activity). The above 5' gene trap cassettes can efficiently mutate genes and can be used to follow the expression of the trapped gene. Optimizing the SA sequence used can further enhance, or regulate, the efficiency of the 5' gene trap cassette. Examples of suitable SA sequences include, but are not limited to: GCAACCAG-TAACCTCTGCCCTTTCTCCTCCATGACAACCAGGT (SEQ ID NO: 6); GATGATGTCATACTTATCCTGTCCT-GTCCCTTTTTTTTCCACAGCT (SEQ ID NO: 7); GGCG-GTCAGGCTGCCCTCTGTTCCCATTGCAGGGAA (SEQ ID NO: 8); TGTCAGTCTGTCATCCTTGCCCCT-TCAGCCGCCCGGATGGCG (SEQ ID NO: 9); TGCTGA-CACCCCACTGTTCCCTGCAGGACCGCCTTCAAC (SEQ ID NO: 10); TAATTGTGTAATTATTGTTTTTC-CTCCTTTAGAT (SEQ ID NO: 11); CAGAATCTTCTTTT-TAATTCCTGATTTTATTTCTATAGGA (SEQ ID NO 12); TACTAACATTGCCTTTTCCTCCTTC-CCTCCCACAGGT (SEQ ID NO: 13); TGCTC-CACTTTGAAACAGCTGTCTTTCTTTTGCAGAT (SEQ ID NO: 14); CTCTCTGCCTATTGGTCTATTTTCCCAC-CCTTAGGC (SEQ ID NO: 15); and ATTAATTACTCTGC-CCATTCCTCTCTTTCAGAGTT (SEQ ID NO: 16). Any of the above SA sequences can be used in conjunction with, for example, SAneopA or SAIRESneopA.

Optionally, the 5' gene trap cassette can be flanked by suitable recombinase sites (e.g., lox P, frt, etc.). In one such embodiment, a recombinase site flanked 5' gene trap cassette is used in conjunction with a second 5' gene trap cassette (present downstream from the 3' recombinase site) that encodes a detectable marker, a different selectable marker, or an enzymatic marker (such as, but not limited to, green fluorescent protein, beta lactamase, TK, blasticidin, HPRT, etc.), and that is preferably not be flanked by the same recombinase sites the first 5' gene trap cassette. In the event that both of the 5' gene trap cassettes are not expressed at acceptable levels (via alternative splicing), the second 5' gene trap cassette (that encodes a detectable marker) can be "activated" by using a suitable recombinase activity (i.e., cre, flp, etc.) in vitro or in vivo to remove the first (recombinase site flanked) 5' gene trap cassette.

5.2.3. Mutagenesis Enhancers

To further enhance the splicing and expression of the exon encoded within a mutagenic 5' gene trap cassette, additional features can be added to the described vectors. For example, a mutagenic mini-exon (see FIG. 4), optionally naturally occurring, can be operatively positioned upstream from the 5' gene trap cassette. This mutagenic mini-exon minimally comprises, in operable combination, a splice acceptor (SA) site, a stretch of exon sequence, and a splice donor (SD). An operative polyadenylation site is not directly associated with the mutagenic mini-exon since the exon is not intended to serve as a terminal 3' exon. The mutagenic mini-exon operates by intercepting the splicing of a cellularly initiated transcript in the area upstream from and in proximity to the SA site of the 5' gene trap/selectable marker. By recruiting the cellular splicing machinery to this region, the SA of the 5' gene trap cassette is more readily recognized and used which, inter alia, effectively enhances the mutagenicity and expression of the 5' gene trap cassette.

Whether or not the mutagenic mini-exon is used in conjunction with a 5' gene trap cassette, it will preferably have 3N+1, or 3N+2 bases in order to alter or change the reading frame of any native gene or exon into which it has been spliced. Alternatively, but less preferably, the mutagenic mini-exons can incorporate stop codons in all three reading frames which would remove the constraint that the exon not contain 3N number of nucleotides. By introducing frame-shift mutations (i.e., inserts having 3N+/−1 bases spanning the SA-SD region of the mutagenic mini-exon), one can also hinder or prevent cellular transcript from "splicing around" an integrated gene trap construct and producing a functional protein product. In such cases, varying the SA and/or SD sequences of the mutagenic mini-exon will produce a corresponding variation in the efficiency of splice intervention (i.e., effective mutagenesis). As such, the presently described mutagenic mini-exons (or mutagenic mini-exons) also provide an effective mechanism for regulating gene expression in a cell or animal. As with essentially all of the mutagenic or regulatory features of the described vectors, the described mutagenic mini-exons can be suitably flanked by recombinase sites to allow for the expedient, and in some cases tissue specific, removal of the mutagenic mini-exon sequence.

Compositional and structural constraints similar to those discussed above can also be used to design mini-exons for use in conjunction with 3' gene trap cassettes (described, infra) that activate cellular gene expression.

Optionally, the mutagenic mini-exon can be used as a combined mutagenic gene trap cassette and sequence acquisition component that operates in place of, or in addition to, the described 5' and 3' gene trap cassettes. In such a construct, the SA of the mutagenic mini-exon is replaced by a promoter element, and the mutagenic mini-exon can serve as a sequence acquisition component that operates independent of the endogenous expression of the trapped gene (in place of, or in addition to, the 3' gene trap cassette). Additionally, the mutagenic mini-exon can be flanked by recombinase sites that allow for the selective or conditional removal of the mutagenic mini-exon.

Additional structural modifications can be employed to enhance the mutagenic effectiveness of the described gene trap vectors. Such modifications include, but are not limited to: 1) modifying/optimizing the sequence at or flanking the branch point sequence and flanking regions of the SA site of the 5' gene trap cassette in order to facilitate splicing of the 5' gene trap cassette by a given target cell (ideally, the SA region will naturally occur in the target cell or be a consensus SA region); 2) placing a terminal 3' exon (SA-exon-polyA/transcription terminator), preferably naturally occurring, operatively positioned upstream from the 3' gene trap cassette (optionally in-between the described 5' and 3' gene trap cassettes); 3) placing a unidirectional transcription terminator sequence operatively positioned upstream from 3' gene trap cassette (optionally in-between the described 5' and 3' gene trap cassettes, and preferably downstream from the terminal 3' exon); and 4) incorporating into the vector in a functional orientation a self-cleaving RNA sequence upstream from the 3' gene trap cassette (and preferably downstream from the 5' gene trap cassette and, optionally, on either side of any naturally occurring terminal 3' exon or unidirectional transcription terminator that may be present in one of the described gene trap constructs) that further ablates the possibility that a cellularly initiated transcript will "splice-around" a vector encoded gene trap element.

Cellular splicing of exogenously introduced, or foreign, exons can also be enhanced by incorporating cassettes encoding small nuclear RNA and/or small nuclear ribonucleoproteins that have been engineered to increase the splicing efficiency of an exogenously introduced gene trap cassette or mutagenic mini-exon cassette.

Several of the above features (e.g., the 3' terminal exon and transcription terminator, etc.) also enhance the efficiency of sequence acquisition by the 3' gene trap cassette by preventing run-on transcription/promoter interference that can hinder the expression of the 3' gene trap cassette. Additionally, particularly where retroviral vectors are employed, the orientation of several of the above features is particularly important given that some of the structural elements would hinder, if not prevent, the expression and packaging of the retroviral RNA genome.

Another embodiment of the present invention contemplates the placement of recombinase sites flanking one or more of the mutagenesis enhancer regions, or any other gene trap or other cassette or portion of the described vectors. Using this arrangement, virtually any portion of the vector that is flanked by recombinase sites can be conditionally activated, or deactivated, by exposing a cell harboring such a construct to the corresponding recombinase activity. Optionally, different mutagenesis enhancer regions such as the mutagenic mini-exon cassette, transcription terminator, and the self cleaving RNA cassette can be flanked by different recombinase sites that will allow the independent modulation or the function of one or both of these components. Using such an arrangement in conjunction with a downstream 5' gene trap cassette mutagenic enhancer sequence, the 5' gene trap can be "activated" by the recombinase-mediated removal of the mutagenic enhancer sequence.

As a rapid means of detecting whether a given integration locus may allow the cell to efficiently "splice-around" a given 5' gene trap cassette, a second 5' gene trap cassette incorporating a different selectable, or enzymatically or fluorescently detectable, marker can be incorporated in tandem with and downstream from the first 5' gene trap cassette. By screening or selecting for the expression of both the first and second 5' gene trap cassettes, one can rapidly determine the extent to which a cell incorporating such a vector might "splice-around" the first 5' gene trap cassette. The second 5' gene trap cassette can also be positioned either upstream or downstream from any mutagenesis enhancer sequences that are present in a given vector in order to determine the effectiveness of the mutagenesis enhancer sequence.

Alternatively, the exon of the second 5' gene trap cassette can encode, for example, the thymidine kinase (TK) gene. Using such constructs, FIAU, for example, can be used to select against cells that "splice-around" the first, or "mutagenic," 5' gene trap cassette. Generally, the second 5' gene trap cassettes are incorporated into the vector downstream from the mutagenesis enhancer sequences and upstream from the 3' gene trap cassette. Optionally, one of the two tandem 5' gene trap cassettes can be flanked by suitably oriented recombinase sites that allow the subsequent and specific removal of the 5' gene trap cassette. Using such a strategy, a first 5' gene trap exon (e.g., encoding neo resistance) may be removed using a suitable recombinase activity to effectively "activate" the splicing and expression of the second 5' gene trap cassette which (especially when it encodes a suitable marker/signal activity such as β-gal, green fluorescent protein, etc.) can be used to track the expression of the trapped gene in tissue and in cells and tissue samples using established methods.

5.2.4. Trans-acting Mutagenic Elements

Another embodiment of the present invention includes vectors that have been engineered to encode and express products that reduce the function or expression of the corresponding unaltered allele by antisense or ribozyme cleavage. For example, such vectors could contain an promoter element, preferably inducible or conditional, that directs an antisense transcript that reads into the portion of the target cell genome that flanks the integrated vector. Presumably, such an inducible promoter would engineered to be present in the integrated provirus in the region 3' of the R region and 5' of the 3'-terminal inverted repeat of the retroviral LTR (for example, at the Nhe I site located within 75 bases of the terminal inverted repeat sequences—this and other restriction sites in the LTR can also be modified to insert a unique, or rare, restriction site). Alternatively, such a promoter can be flanked by recombinase sites and placed in a reverse orientation (relative to the LTR) and subsequently activated (by recombinase-mediated "flipping") using a suitable recombinase activity. In general, antisense strategies or features similar to those described in U.S. Pat. No. 5,679,523, herein incorporated by reference, can be incorporated into the presently described vectors. Where the use of ribozymes or catalytic RNAs are contemplated, ribozymes can be engineered that are transcribed and appended to (via splicing or cotranscription), and preferably targeted to, cellularly encoded transcripts. Ribozyme methods are also adaptable to the recombinase strategy described above.

As an alternative means of generating functionally homozygous mutant cells, the described mutagenic vectors can be utilized in conjunction with traditional mutagenic methodologies (i.e., radiation, chemical mutagenesis, UV light, bulky addition products, deletion mutagenesis, insertional mutagenesis, frame shift mutagenesis, and transition and transversion mutagens, etc.). Appropriately mutagenized cells, for example a series of target cells containing large and preferably overlapping regions of deleted chromosomal DNA, increase the probability that a given mutational event obtained with the described vectors will effectively manifest itself as a homozygous knock out event.

5.2.5. 3' Gene Trap Cassette

The presently described 3' gene trap cassette comprises, in operative combination, a promoter region that mediates the expression of an exon, and an operative splice donor (SD) sequence that defines the 3' end of the exon. After integration into the target cell chromosome, the transcript expressed by the 3' gene trap promoter is spliced to a splice acceptor (SA) sequence of a trapped cellular exon located downstream of the integrated 3' gene trap cassette. Thus, a fusion transcript is generated comprising the exon of the 3' gene trap cassette and any downstream cellular exons the most 3' of which has a polyadenylation signal.

The fusion transcript can be identified by a variety of methods known to those of skill in the art at any level of expression, i.e., as a heterogenous nuclear RNA, as a messenger RNA, as a protein, etc. For example, one may perform polymerase chain reaction using a primer pair specific for the exon of the 3' gene trap cassette and the polyA tail of the transcript. Or, for example, one may use an exon in the 3' gene trap cassette which encodes an epitope which can be identified in an antibody screen, i.e., epitope tagging. Other screening methods known in the art include, but are not limited to, hybridization (on solid support or in solution, etc.) with a probe specific for the exon of the 3' gene trap cassette. When screening on the protein level, one may carry out the screen in any cellular location, e.g., one may screen for secreted proteins encoded by the fusion transcript. Or, for example, one may use a first exon which encodes a secretion signal, thus making the host cells secrete many or all fusion peptides encoded by the fusion transcripts. All screening methods may also be modified to render them specific for the trapped exons and the proteins and polypeptides they encode, i.e., PCR primers, hybridization probes or antibodies specific for a particular gene or class of genes may be used to screen. Or, for example, one may screen based on a posttranslational modification, e.g., one may screen with an antibody specific for certain or all glycoproteins.

As described above, the 3' gene trap cassette contains a promoter that directs the expression of one or more exons (optionally encoding one or more open reading frames) that are followed by a splice donor sequence (FIG. 1). Any number of transcriptional promoters and enhancers may be incorporated into the 3' gene trap cassette including, but not limited to, cell or tissue specific promoters, inducible promoters, the herpes simplex thymidine kinase promoter, cytomegalovirus (CMV) promoter/enhancer, SV40 promoters, PGK promoter, regulatable promoters (e.g., metallothionein promoter), adenovirus late promoter, vaccinia virus 7.5K promoter, avian (i.e., chicken, etc.) beta globin promoter, histone promoters (e.g., mouse histone H3-614, etc.), beta actin promoter (preferably chicken), metallothionein promoters (preferably mouse metallothionein I and II), the cauliflower mosaic virus 35S promoter and the like, as well as any permutations and variations thereof, which can be produced using well established molecular biology techniques (see generally, Sambrook et al. (1989) *Molecular Cloning Vols. I–III*, Cold Spring Harbor Laboratory Press, Cold Spring Harbor, N.Y., and *Current Protocols in Molecular Biology* (1989) John Wiley & Sons, all Vols. and periodic updates thereof, herein incorporated by reference). Promoter/enhancer regions can also be selected to provide tissue-specific expression or inducible expression.

Preferably, the exon (or exons) of the 3' gene trap cassette has been designed to mimic an exon of a gene, preferably a first exon. Generally, the exon or exons (and part of the intron following the exon(s)) and splice donor sequence are derived from a naturally occurring gene; however, synthetic exons designed to mimic a real exon can also be used. For example, such exons might be designed and constructed de novo or by modifying existing exons to incorporate a high efficiency, or consensus, ribosome binding site or to add an IRES sequence 5' to the translation initiation codon of an open reading frame or exon, to create an open reading frame, to optimize codon usage, to engineer one or more restriction sites that do not alter the amino acid sequence encoded by the open reading frame, or to engineer an alternative or consensus splice donor sequence into the exon.

Presently described vectors use a 3' gene trap cassette that-employs an exon of non-prokaryotic origin, i.e., an exon obtained from a eukaryotic organism. Exons useful for the 3' gene trap cassette of the invention do not encode an antibiotic resistance activity, or other selectable marker, activity (e.g., an antibiotic resistance gene). As discussed herein, 3' gene trap cassettes incorporating open reading frames of noneukaryotic origin typically display a markedly reduced efficiency of 3' exon trapping. Consequently, vectors employing the presently described 3' gene trap cassette greatly increase the number of target genes that can be trapped and rapidly identified by gene trap sequence tagging.

Accordingly, the exon of the 3' gene trap cassette (including the SD site) is preferably derived from nucleotide sequence that is similar or homologous to nucleotide sequence that is native to an eukaryotic cell, or, possibly, an animal or plant virus, or naturally occurs in, the target cell, or the genome of cells from a related species, genus, order, class, phylum, or kingdom. For example, an exon from a human gene may be used in a 3' gene trap cassette that is used in mouse cells and an exon from a mouse gene may be used in a 3' gene trap cassette that is used in human cells. For the purposes of the present invention, a homologous sequence is defined as a nucleic acid sequence that is capable of binding to a target sequence under highly stringent conditions such as, for example, hybridization to filter-bound DNA in 0.5 M $NaHPO_4$, 7% sodium dodecyl sulfate (SDS), 1 mM EDTA at 65° C., and washing in 0.1×SSC/ 0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3), or possibly under less stringent conditions, such as, for example, moderately stringent conditions, e.g., washing in 0.2×SSC/0.1% SDS at 42° C. (Ausubel et al., 1989, supra). Optionally, the exon is isogenic to sequence in the target cell genome.

Exons suitable for the 3' gene trap cassette of the present invention may also be obtained by combining naturally occurring exons, or by combining fragments of naturally occurring exons, or by combining fragments of naturally occurring exons with synthetic sequences which may be consensus sequences of naturally occurring exons. For example, when using an exon found in the genome of a eukaryotic organism that is not the first exon of a gene, one may render it useful for the 3' gene trap cassette of the present invention by adding a suitable transcription initiation sequence to the 5' end of the exon.

Where the target cell genome encodes a gene identical to (or corresponding to) the exon of the 3' gene trap cassette, the naturally occurring gene will preferably not be expressed by the target cell at levels that substantially interfere with the amplification and sequencing of the trapped exon sequences in the target cells. For the purposes of the present disclosure, the term "substantially interfere with the amplification and sequencing" shall refer to the fact that the endogenous expression of the naturally occurring exon may hinder but shall not prevent the amplification and sequencing of the trapped exon sequence by 3' RACE protocols, or, optionally, by conventional cloning and sequencing. Additional methods of circumventing this potential complication include the incorporation of an unique sequence within the otherwise naturally occurring exon of the 3' gene trap cassette that can be used as PCR priming site, or to employ a 3' gene trap cassette having an exon that does not naturally occur in the target cell genome. Yet another method of circumventing this potential complication is to use an exon in the 3' gene trap cassette that is obtained from an inducible gene, e.g., stress genes. Preferably, in this embodiment, the cells in which the 3' gene trap cassette is used would be maintained under conditions so that the gene from which the exon is obtained is not or barely induced, if the gene is present in those cells.

The exon of the presently described 3' gene trap cassette may or may not contain a translation start site and/or an open reading frame. Optionally, any open reading frame(s) that may be present in the exon can be engineered to incorporate codons that have been optimized to reflect the preferred codon usage of the host cell.

Given that the exon of the presently described 3' gene trap cassette preferably comprises sequence native to an eukaryotic, or preferably mammalian, cell, the exon will typically not constitute a marker encoding a protein having an antibiotic resistance activity (such as neo, amp, e.g., β-lactamase, tet, kan, and the like) or otherwise confers selectable drug resistance or sensitivity to the host cell (although such a marker can optionally be appended to, for example, the 5' region of the exon). For the purposes of the present invention, a gene or gene product is capable of "conferring" antibiotic resistance if a gene encodes a gene product having an activity that provides a selective growth to a prokaryotic or eukaryotic cell expressing the antibiotic resistance gene in media containing appropriate concentrations of the corresponding antibiotic.

Alternatively, the exon will generally not encode an enzymatic activity, or reporter gene, that mediates selectable detection via a well known conventional chromogenic or fluorescent assay (e.g., β-galactosidase, alkaline phosphatase, or horse radish peroxidase) that is not native to the, preferably mammalian, target cell. Additionally, the presently described vectors shall preferably not contain regions of targeting DNA sequence (i.e., for directing gene targeting of the 3' gene trap cassette to a specific genetic locus via homologous recombination) flanking the described 3' gene trap cassette.

Moreover, given that splice donor efficiency can be influenced by intron sequences downstream from the splice donor site, the presently described 3' gene trap cassette can optionally be engineered to contain between about one base and about several thousand bases of intron sequence adjacent and 3' to the splice donor sequence.

5.3. Applications of the Described Vectors

Vectors incorporating:the described 3' gene trap cassettes are characterized by a marked improvement in the efficiency of 3' gene trapping. As such, another embodiment of the present invention is a 3' gene trap cassette, and vectors incorporating the same, that are characterized by the capability of trapping 3' exons with at least about 15 percent of the efficiency with which a similarly situated SAβgeo 5' gene trap cassette (or SAneo 5' gene trap cassette) traps 5' exons, preferably, at least about 25 percent, more preferably at least about 40 percent, more preferably at least about 60 percent, and most preferably at least about 85 percent. For the purposes of the present invention, a similarly situated gene trap cassette is a cassette that is present in a similar orientation within a similar vector. Alternatively, similarly situated gene trap cassettes may both be present in the same vector.

Any of a variety of quantitative measurements are available to those skilled in the art and can be used to calculate the relative efficiency of the respective 3' and 5' gene trap cassettes as well as the number of genes that can be effectively trapped. For example, one can determine the percentage of target genes identified by the presently described 3' gene trap cassette relative to the percentage of target genes identified by 5' gene traps such as SAβgeo or SAneo and selected using, for example, the antibiotic G418. Alternatively, the percentage of identifiable 3' gene trap events can be compared to the percentage of target cells rendered antibiotic resistant or chromogenically identifiable by SAβgeo-mediated 5' gene trap events.

The functional efficiency of the presently described 3' gene trap cassette can also be quantified by the absolute number of independent gene trap events characterized using the vector. Generally, the presently described vectors allow for the expedient trapping of at least about one to about several hundred genes, typically at least about 1,000 different genes, more typically at least about 3,000, preferably at least about 10,000 genes, more preferably at least about 25,000 genes, more preferably at least about 50,000 genes, and most preferably at-least about 55,000 genes up to the maximum number of genes present in a given cell or cell type. For example, murine cells are thought to encode between about 60,000 to 100,000 genes or more.

Another measure of gene trapping efficiency is the number of distinct cellular exons that can be trapped. Typically, the presently described 3' gene trap cassette will trap cellular 3' exons with sufficient efficiency to enable the facile detection, screening, and identification of at least about 10,000 distinct 3' gene trapped cellular exons (generally representing approximately between about 7,500 to 9,500 different genes—the number is typically smaller because independent integration events can occur within different introns/exons within the same gene), preferably at least about 15,000 distinct 3' gene trapped cellular exons, more preferably at least about 25,000 distinct 3' gene trapped cellular exons, and most preferably at least about 50,000 distinct 3' gene trapped cellular exons up to between about 70 and about 100 percent of the genes present in the mammalian genome.

5.3.1. Gene Trapped Libraries of Cells

Given the number of genes that can be rapidly characterized using the present vectors, additional embodiments of the present invention include gene trapped libraries of cultured animal cells that stably incorporate the presently described 3' gene trap cassette. The presently described libraries may be made by a process comprising the steps of treating (i.e., infecting, transfecting, retrotransposing, or virtually any other method of introducing polynucleotides into a cell) a population of cells to stably integrate a vector containing the 3' gene trap cassette, identifying or otherwise selecting for stably transduced cells, and identifying the trapped 3' cellular exons. In a preferred embodiment, the animal cell libraries comprise mammalian cells, and in a particularly preferred embodiment, the mammalian cells are embryonic stem (ES) cells. Preferably, such libraries are constructed such that each mutated cell in the library harbors a single identifiable 3' gene trap vector/event (although mutated cells harboring multiple gene trap vectors are also contemplated by the present invention).

In an additional embodiment of the present invention, the individual mutant cells in the library are separated and clonally expanded. The isolated and clonally expanded mutant cells are then analyzed to ascertain the DNA sequence, or partial DNA sequence, of the insertionally mutated host gene. Thus, the invention further provides for the sequencing of at least a portion of every gene mutated in the library. The resulting sequence database subsequently serves as an index for the library. In essence, every group of clonally expanded cells in the library is individually catalogued using the partial sequence information. The resulting sequence is specific for the mutated gene since the present methods are designed to obtain sequence information from exons that have been spliced to the 3' gene trap cassette. The resulting sequence database can be used to identify the mutated gene of interest, or, alternatively, represents a powerful tool for the identification of novel genes. Once identified, the corresponding mutant cell may be taken from the library and studied further as described below.

Generally, indexed libraries of isolated cells, or individual cell types (e.g., ES cells), that have been mutated using vectors incorporating the described 3' gene trap cassette will comprise a collection of at least about 50 different isolated mutant cell culture lines, typically at least about 100, more typically, at least about 500, preferably at least about 1,000, more preferably at least about 5,000, more preferably at least about 10,000, more preferably at least about 25,000, and even more preferably at least about 40,000 up to about one to five hundred thousand different isolated and characterized mutant cell culture lines or more. Preferably, the genomes of the different mutant cell cultures present in a given library are essentially identical (e.g., derived from a common source or inbred strain) except for the location of the inserted gene trap cassette, or vector incorporating the same.

Ideally, the scope of mutagenesis is the entire set of genes that can be trapped in the target cell line. By increasing the redundancy of the library, the resulting sequence database will ideally contain an essentially complete representation of the genes that can be trapped in the target cell. For the purposes of the present invention, the term "essentially complete representation" shall refer to the statistical situation where there is generally at least about an 80–95 percent probability that the genomes of the cells' used to construct the library collectively contain a stably inserted 3' gene trap cassette in at least about 70 percent of the genes that can be trapped in the target cell genome, preferably at least about 85 percent, and most preferably at least about a 95 percent of the genes that can be trapped as determined by a standard Poisson distribution (and assuming that a given vector integrates into the genome nonspecifically).

The broad genomic coverage afforded by the present vectors also allows for the large-scale mutagenesis of the target cell genome. Typically, such a library of mutated target cells will comprise a collection of mutated cells, or isolated cultures thereof, that collectively represent at least one 3' gene trap mutation (mediated by the described 3' gene trap cassette or vector comprising the same) in each chromosome present in the target cell genome, preferably at least about 2 to 3 independent gene trap mutations per chromosome will be collectively present in the library, more preferably at least about 10 independent gene trap mutations per chromosome are represented, and most preferably at least about 500 independent gene trap mutations per autosomal chromosome (minus the sex chromosomes), and/or up to about 70 to 90 percent, or even an essentially complete representation of the genes in the genome will be collectively represented in the library.

The presently described invention allows for large-scale genetic analysis of the genome of any organism/cell that can be transduced with the described vectors or for which there exists cultured cell lines. Accordingly, the described libraries can be constructed from any type of cell that can be transfected by standard techniques or transfected with a recombinant vector harboring the described 3' gene trap cassette. As such, the presently described methods of making, organizing, and indexing libraries of mutated animal cells are also broadly applicable to virtually any eukaryotic cells that may be genetically manipulated and grown in culture.

Where mouse ES cells are used to construct the library, and preferably early passage ES cells, the library becomes a genetic tool for the comprehensive functional study of the mouse genome. Since ES cells can be injected back into a blastocyst and incorporated into normal development and ultimately the germ line, the mutated ES cells of the library effectively represent a collection of mutant transgenic mouse strains (see generally, U.S. Pat. No. 5,464,764 issued Nov. 7, 1995, herein incorporated by reference).

A similar methodology can be used to construct virtually any non-human transgenic animal (or animal capable of being rendered transgenic), or transgenic plants. Such non-human transgenic animals may include, for example, transgenic pigs, transgenic rats, transgenic rabbits, transgenic cattle, transgenic goats, and other transgenic animal species, particularly mammalian species, known in the art. Additionally, bovine, ovine, and porcine species, other members of the rodent family, e.g., rat, as well as rabbit and guinea pig and non-human primates, such as chimpanzee, may be used to practice the present invention.

Transgenic animals and cells produced using the presently described library and/or vectors are useful for the study of basic biological processes and the development of therapeutics and diagnostics for diseases including, but not limited to, aging, cancer, autoimmune disease, immune disorders, alopecia, glandular disorders, inflammatory disorders, ataxia telangiectasia, diabetes, arthritis, high blood pressure, atherosclerosis, cardiovascular disease, pulmonary disease, degenerative diseases of the neural or skeletal systems, Alzheimer's disease, Parkinson's disease, asthma, developmental disorders or abnormalities, infertility, epithelial ulcerations, and viral and microbial pathogenesis and infectious disease (a relatively comprehensive review of such pathogens is provided, inter alia, in Mandell et al., 1990, "Principles and Practice of Infectious Disease" 3rd. ed., Churchill Livingstone Inc., New York, N.Y. 10036, herein incorporated by reference). As such, the described animals and cells are particularly useful for the practice of functional genomics (similar libraries, and methods of making and screening the same, are discussed in U.S. application Ser. No. 08/942,806, filed Oct. 2, 1997, now U.S. Pat. No. 6,207,371, the disclosure of which is herein incorporated by reference in its entirety).

5.3.2. The Acquisition of DNA Sequence Information

The sequencing of cDNA libraries has provided many hundreds of thousands of expressed sequence tags (ESTs). These sequence tags are typically thought to identify genes or the coding portion of DNA. Since genes are thought to code for most, if not all, potential drug targets, there has been a rush to obtain ESTs identifying all mammalian genes. However, in spite of the wealth of sequence data generated thus far, many genes have proven difficult to identify using established cDNA methods because many genes are not expressed, are expressed at very low levels, are expressed only in specific cell types, or are only transiently expressed. Given that gene trapping can identify genes independent of their endogenous expression levels gene trapping is an important tool for gene discovery (as demonstrated by the large number of novel sequences that have been identified using the described vectors). Like EST technology, one potential limitation of 5' gene trap vectors (vectors designed to trap 5' exons) is that only expressed genes are typically trapped. Accordingly, particularly for the purposes of gene discovery, ES cells are particularly preferred target cells because ES cells are thought to be generally promiscuous in the expression of most genes. Given this promiscuity, then most genes could be trapped in ES cells using the presently described vectors. To test the percentage of genes that can be detected as expressed in ES cells, 23 ESTs from the GenBank dbest database were selected at random, and primers were synthesized that would identify the genes by PCR. When these primers were used in RT-PCR assays using ES cell RNA, all 23 sets of primers produced product. This indicates that transcripts for all 23 genes could be detected in ES cells. Given that the 23 ESTs screened were selected at random, it is likely that they are largely representative of genes in general and indicate that a majority of genes that are expressed in other cell types at sufficiently high levels to have been identified by sequencing of conventional cDNA libraries are also expressed in ES cells and are thus presumably identifiable using SAselectable marker poly A (5' gene trap) vectors.

However, in those instances where genes are either not expressed or only poorly expressed, a 3' gene trap cassette must be utilized to trap and identify the genes. In addition, 3' gene trap cassettes enable the rapid procurement of DNA sequence data from the trapped gene by automated means.

Vectors designed to trap 3' exons have made it possible to produce large numbers of mutations and rapidly identify the genes that have been mutated. However, a limitation of initial versions of such vectors is that selectable marker genes used in the 3' gene trap are inefficiently utilized by the splicing machinery of most eukaryotic cells. As a consequence, vectors employing a 3' gene trap cassette that employ an exon encoding an activity conferring antibiotic resistance only allow the facile and efficient gene trapping and identification (using 3' RACE) of a relatively small proportion of the genes in the genome. Additionally, the inherent inefficiency of selecting for trapped 3' exons limits the total number of genes that can be analyzed using such methods. Consequently, prior to the present invention, only a small portion of the cellular genome had been effectively trapped/mutagenized using antibiotic selection-mediated 3' exon trapping.

The presently described vectors incorporate a 3' gene trap cassette that typically allows several fold to more than an order of magnitude greater number of genes to be trapped and identified by exon sequence as compared to initial 3' gene trap vectors that utilize an exon encoding a selectable marker activity.

The presently described vectors can also incorporate 3' and/or 5' gene trap cassettes that are engineered to increase the probability of identifying the 5' ends of the open reading frames of genes. This is significant because the 5' ends of genes often code for the signal sequence that is found in secreted and transmembrane proteins. This group of genes is highly enriched for potential protein therapeutics and drug targets. Given that 5' noncoding sequences average about 100 bp in length and the average length gene trap sequence is about 500 bp, gene trapped sequences generated using the presently described vectors will typically identify the 5' portion of the tagged open reading frame. This is especially valuable since 5' ends of genes can be difficult to obtain due to complicating factors such as high GC content, secondary structure, and reverse transcriptase's lack of processivity.

When a large number of gene traps in known genes were made and identified using the described vectors, 3' of the gene trap sequence tags that matched cDNA sequences in GenBank contained the same or additional 5' sequence. This confirms that the described 3' gene trap cassette can be used to identify and characterize the 5' termini of genes. In fact, the gene trap methods of the present invention identify the 5' end of genes better than or equal to other methods described to date.

One of the major challenges in the field of genomics remains the isolation and cloning of full length cDNAs for all genes. To date, this has required the production of cDNA from a wide variety of tissues, followed by the subsequent sequencing of the individual cDNAs. As described above, using such methods it can be very difficult to obtain the 5' ends of cDNAs. Additionally there is the problem that in order to obtain a complete repertoire of cDNAs, individual cDNA libraries must made from essentially every differentiated cell type and at every developmental time point because genes must be expressed in order to be cloned as ESTs.

As discussed above, the presently described vectors can be used for the creation of cDNA libraries. When introduced to cells in culture, the 3' gene trap cassette produces transcripts of genes independent of whether or not they are normally expressed in that cell type. The expression levels of the various trapped genes are normalized by the inserted promoter so that even genes that are only expressed at very low levels are identified. Using the presently described methods and vectors, one can obtain broad cDNA coverage of the target cell genome from a single library without having to independently produce multiple cDNA libraries from multiple cell types that were grown under multiple conditions.

The presently described 3' gene trap cassette can be inserted into the genome of tissue culture cells, for example, and methods (e.g., PCR) can be used that only allow cDNA arising from trapped genes to be subcloned into the cDNA library. These methods will increase coverage of the cDNAs produced while substantially decreasing the labor involved to produce the libraries. As discussed above, the presently described methods are also particularly useful in obtaining the 5' ends of genes, and thus optimize the chances of obtaining full length cDNAs. Examples of variables that can be used to alter the variety and number of trapped cDNAs produced using the described vectors include, but are not limited to, adjusting the multiplicity of infection, and producing cDNAs from infected target cells that have not been subject to a period of selective culture in order to select for cells incorporating and expressing an exogenously introduced selectable marker. The resulting gene trapped cDNA libraries can be sequenced to produce a multiplicity of gene trapped coding regions of genes, that can be used for bioinformatics, gene expression studies both in situ and in vitro (i.e. hybridization studies, gene chips (which can also use oligonucleotide sequences corresponding to the trapped gene sequences), etc.), and the production of gene trap sequence databases from a variety of animals and plants. These gene trap sequences can be utilized as probes directly, or oligonucleotide sequences corresponding to the gene trap sequences can be used screen libraries by hybridization or PCR. Also, gene trap sequences identified using the disclosed vectors can be incorporated into cloning vectors that direct the expression of the gene trap sequences. For the purposes of the present disclosure, an isolated polynucleotide sequence having, containing, or otherwise incorporating such a gene trap sequence (or an oligonucleotide sequence derived therefrom) shall mean any and all isolated polynucleotides or vectors minimally incorporating, or comprising, a contiguous stretch of the described cDNA gene trap sequence (or an oligonucleotide sequence derived therefrom) inclusive of any additional naturally occurring or recombinant sequences that may flank the described gene trap sequence present in such isolated polynucleotides or vectors.

Given the speed and efficiency with which DNA (and corresponding amino acid) sequence information can be obtained using the described methods and vectors, it is clear that they provide important tools for conducting genetic screens in any cell (including primary and secondary cells) or cell line that contains splicing machinery and genes containing introns. The presently described gene trap vectors represent a particularly important technological breakthrough because the described 3' gene trap cassette allows for the rapid identification of roughly 13 fold (as empirically determined) more genes than can be efficiently obtained using conventional 3' gene trap vectors that rely upon gene trapping as detected by antibiotic selection. Combined with the frequency of obtaining novel gene sequences, the observed increase in identifiable gene trap targets will provide sequence information for large numbers of novel genes and gene sequences. Additionally, when ES cells are targeted, each of these novel sequences represent both newly identified gene (and potential drug or drug target) and a "knockout" cell and a potential "knockout" embryo or animal.

The rapid sequence acquisition features of the presently described methods, libraries, cells, and animals are well suited for rapidly identifying the molecular/genetic basis for disease as well as genetically determined advantages such as prolonged life-span, low cholesterol, low blood pressure, resistance to cancer, low incidence of diabetes, lack of obesity, or the attenuation of, or the prevention of, all inflammatory disorders, including, but not limited to coronary artery disease, multiple sclerosis, rheumatoid arthritis, systemic lupus erythematosus, and inflammatory bowel disease. Given the wide coverage provided by the large number of target genes, a particularly useful application of the described techniques involves the characterization and analysis of coding region single nucleotide polymorphisms (cSNPs).

5.4. Methods of Introduction

The presently described 3' gene trap cassette is preferably introduced into target cells as a structural component of any of a wide range of vectors that can be specifically or nonspecifically inserted into the target cell genome (recombinase systems can also be used to insert the 3' gene trap cassette). Suitable vectors that can be used in conjunction with the presently disclosed features include, but are not limited to, herpes simplex virus vectors, adenovirus vectors, adeno-associated virus vectors, retroviral vectors, lentiviral vectors, pseudorabies virus, alpha-herpes virus vectors, and the like. A thorough review of viral vectors, particularly viral vectors suitable for modifying nonreplicating cells, and how to use such vectors in conjunction with the expression of polynucleotides of interest can be found in the book *Viral Vectors: Gene Therapy and Neuroscience Applications* Ed. Caplitt and Loewy, Academic Press, San Diego (1995).

Where retroviral vectors are used to deliver the presently described 3' gene trap cassette, the retroviral vectors can be used in conjunction with retroviral packaging cell lines such as those described in U.S. Pat. No. 5,449,614 ("'614 patent") issued Sep. 12, 1995, herein incorporated by reference. Where non-mouse animal cells are to be used as targets for generating the described libraries, packaging cells producing retrovirus with amphotropic envelopes will generally be employed to allow infection of a broad range of host cells. Alternatively, pantropic packaging cell lines such as, but not limited to, the cell line 293/GPG (Ory et al., 1996, Proc. Natl. Acad. Sci., USA, 93:11400–11406, and U.S. applic. Ser. No. 08/651,050, abandoned Aug. 27, 1998, herein incorporated by reference) can be used to package the described vectors, or a suitable viral, e.g., retroviral, receptor gene can be transfected into the non-murine, e.g., human, target cells.

Additionally, the described retroviral vectors can be packaged in conjunction with chimeric integrase molecules as described in U.S. application Ser. No. 08/907,598, now U.S. Pat. No. 6,139,833, herein incorporated by reference. Typically, the LTRs used in the construction of the packaging cell lines are self-inactivating. That is, the enhancer element is removed from the 3' U3 sequences such that the proviruses resulting from infection would not have an enhancer in either LTR. An enhancer in the provirus may otherwise affect transcription of the mutated gene or nearby genes. Typically, the gene trap cassettes of the described retroviral vectors are present in an orientation opposite the normal functional orientation of the retroviral LTRs.

An additional advantage of using viral, and particularly retroviral, infection (e.g., biological methods) to deliver recombinant viral vectors incorporating, inter alia, the 3' gene trap cassette is that viral infection is more efficient than standard nonbiological methods of delivering genetic material to target cells. Where recombinant genetic material is delivered by retroviral infection, the recombinant RNA genome of the retrovirus is reverse transcribed within the target cell, and the retroviral integrase packaged within the infecting virus subsequently mediates the essentially non-specific integration of the vector (and 3' gene trap cassette) into the target cell genome. Accordingly, additional embodiments of the present invention include methods of inserting recombinant vectors incorporating the described 3' gene trap cassette that are mediated by integrase or recombinase activities that are either exogenously added to. the target cell, or do not naturally occur within the target cell.

Representative retroviral vectors that can be adapted to incorporate the presently described 3' gene trap cassette are described, inter alia, in U.S. Pat. No. 5,521,076, and U.S. applications Ser. No. 08/942,806, filed Oct. 2, 1997, now U.S. Pat. No. 6,207,371, and Ser. No. 08/907,598 filed Aug. 8, 1997, now U.S. Pat. No. 6,139,833, (which further disclose screening protocols that can be used to assay for specific gene trap events either biochemically or phenotypically) the disclosures of which are herein incorporated by reference.

Typically, the orientation of the gene trap cassettes incorporated into retroviral vectors is opposite to that of normal retroviral transcription; however, retroviral vectors are also contemplated where one or more gene trap cassettes are incorporated in the same orientation as normal retrovirus transcription. Typically, the reason for placing a gene trap cassette in an opposite orientation relative to the LTRs is that the presence of engineered control elements such as poly-adenylation signals, splice sites and the promoters, can interfere with the proper transcription of the retroviral genome in the packaging cell line, and subsequently reduce retroviral titers.

Additionally, since a 'cryptic' splice donor sequence is found in the inverted LTRs, this splice donor can be removed by site specific mutagenesis so that it does not adversely effect trapping related splicing events. Optionally, the LTR promoter and/or enhancer function can be inactivated by deleting all or a portion of the promoter and/or enhancer sequences.

5.5. Molecular Genetic Applications 5.5.1. Gene Activation

Another embodiment of the present invention is the use of the 3' gene trap cassette to screen for both gain or loss of function in animals, e.g., mice, and cultured cells. When vectors are used that incorporate a 3' gene trap having an exon that lacks a translation start site, a given target gene can be either over expressed or insertionally inactivated (mutated) depending on where the vector has integrated within the gene. If the vector lands in an intron preceding the start of translation, it can cause over expression of the full open reading frame encoding the cellular protein. Using these types of trapping events one can conduct genetic screens based upon gene over expression. These screens could be done in cell culture or in mice, for example, in order to discover genes that play significant roles in disease processes. For example, these screens could be used to identify oncogenes by introducing the 3' gene trap cassette into primary embryo fibroblasts and selecting for an ability to grow in soft agar. Alternatively, assaying for cells able to escape cellular senescence would also allow the identification of potential oncogenes.

In order to demonstrate that the present vectors can be used to select for trapping events that result in gene expression (or over expression), an experiment was conducted to determine whether genes could be trapped that allow expression of factors that promote ES cell differentiation. Large numbers of genes were trapped in cell culture on tissue culture plates. Multiple plates were infected in parallel and the resulting plates were observed for ES cell differentiation. Some plates showed almost no differentiation whereas some plates would have 100% differentiated ES cells. This differentiation is likely the result of the expression of a gene that is either a differentiation factor or causes the ES cells to produce a differentiation factor and pump it into the media resulting in differentiation of all the cells on the dish. Importantly, this also demonstrates that the 3' gene trap system can be used to activate and screen for secreted molecules that produce specific biological responses by testing supernatants of the gene trap pools. Screening for ES cell differentiation factors is one example but this technique can be used to identify secreted molecules involved in any cellular response of interest. One could for example screen for secreted molecules that induce apoptosis or hematopoietic cell differentiation.

Given the increased expression afforded by the presently described 3' gene trap cassette, an additional application of the presently described 3' gene trap cassettes is gene activation. For example, after suitable animal cells are treated or infected with vectors that incorporate the described 3' gene trap cassette, if the vector integrates into the 5' intron of an otherwise quiescent gene, the gene can be "activated" and over expressed by the regulatory elements, e.g., enhancer/promoter elements incorporated into the 3' gene trap cassette. Using such nontargeted, nonspecific, or biased nonspecific (see U.S. applic. Ser. No. 08/907,598, now U.S. Pat. No. 6,139,833,) gene activation, modified animal cells, including human cells, can be produced that over express any of a wide variety of natural cellular products.

Products that are particularly deemed useful for such application include normally secreted molecules or hormones such as, but are not limited to, erythropoietin (epo), tPA, cytokines, interleukins, tumor suppressors, chemokines, secreted molecules, G-CSF, GM-CSF, nerve growth factor (NGF), ciliary neurotropic factor (CNTF), brain-derived neurotropic factor (BDNF), interleukins 1–2 and 4–14, tumor necrosis factor-α (TNF-α), α or γ interferons and the like, leptin, and factors VIII and IX.

The activation of quiescent genes, over expression, or abnormal expression of genes by the 3' gene trap cassette can also be used to study gene function within an organism. Gene over expression may be used to study gene function, and by trapping genes with the 3' cassette, genes can be over expressed within an organism. The over expression may cause a phenotype in the organism that sheds light on the function of the gene. For example, the specifically described retroviral vector contains the PGK promoter which is ubiquitously expressed. When a gene is trapped in ES cells and the ES cells are subsequently used to make mice, the mice will over express the trapped gene ubiquitously. Further modifications could be made for instance to use a promoter that is tissue-specific rather than the PGK promoter in order to over express the trapped gene in a tissue-specific manner. The albumin promoter could be used for liver-specific over expression. Additionally, a signal sequence could be added to the 3' trapping cassette to cause secretion of the trapped gene's protein product from the cell into the extracellular space, into the bloodstream, or mammary excretions. This could facilitate the understanding of gene function.

Since over expression is one possible outcome of a gene trap event using the 3' gene trap cassette, it could prove useful to be able to remove the 3' trap/over expression component. This can be accomplished by flanking any essential component of the 3' trap cassette (essential components may include the promoter, the exon, the splice donor, the intronic sequence or the entire cassette) with recombinase sites such as those recognized by the flp or cre recombinases. In this way, the addition of the corresponding recombinase in cells or in the organism allows one to conditionally reverse or remove over expression as desired.

For gene activation, a generic 3' gene trap cassette can be employed that incorporates an exon that is native to, or compatible with the biology of, the target cell, or a specific 3' gene trap cassette can be constructed that utilizes a specific exon and splice donor site from a known gene. Optionally, given that gene activation using 3' gene traps typically requires that the vector integrate or insert upstream (5') from the translation start site of the activated gene, the gene activation exon will preferably not incorporate a functional translation start site (IRES or Kozak sequence), or will only incorporate a nominally functional (or cryptic) translation start site capable of mediating only incidental levels of translational activity. Alternatively, the incorporation of an internal ribosome entry site into the exon can result in the over expression of the 3' gene trapped, or activated, gene.

Where a fusion product between the 3' gene trap exon and a downstream cellularly encoded exon (e.g., that only encodes a particular domain of the protein-product of the "activated" gene) is desired, the gene trap vector will typically incorporate a functional translation start site or internal ribosome entry site and translation start site.

Alternatively, in those instances where the described vectors integrate downstream from the translation start site, the gene will be mutated, and screens to detect such loss of function can be employed. An example of this approach would be to mutate fibroblasts, for example, with the present vectors and screen for hits that allow growth in soft agar. In this way genes encoding tumor suppressors could be identified. Although only 1 of 2 alleles will typically be trapped, the genome of cells in culture is often unstable and, through selection, events can be found in which the second allele is lost. This makes it possible to also screen for recessive phenotypes.

5.5.2. Function-Based Gene Discovery

The gene activation capabilities of the presently described vectors have further application for selective gene discovery. For example, proliferation deficient cells (e.g., tumor suppressor or DNA repair knockout cells, etc.) can be infected with the presently described gene activation vectors. The infected cells can subsequently be screened for cells/colonies that display a partially or fully corrected proliferation phenotype. When cells displaying the corrected phenotype are identified, the "activated" genes responsible for correcting the proliferation deficient phenotype can be rapidly identified by DNA sequencing using, for example, 3' RACE. Typically, genes that partially or fully correct a DNA repair mutation (mutations often associated with cancer in animals and humans), are more likely to encode a tumor suppressor, or possibly oncogene, activity (see generally, Selten et al., 1985, EMBO J., 4(7):1793–1798).

Conversely, cancerous or transformed cells (or cell lines) can be infected with the described gene activation vectors and subsequently subject to various cytotoxic agents that are toxic to growing, or rapidly growing, cells (see generally Wilson et al., 1986, Cell, 44:477–487; Stephenson et al., 1973, J. Virol., 11:218–222; Sacks et al., 1979, Virology, 97:231–240; Inoue et al., 1983, Virology 125:242–245; Norton et al., 1984, J. Virol., 50:439–444; Cho et al., 1976, Science, 194:951–953; Steinberg et al., 1978, Cell 13:19–32; Maruyama et al., 1981, J. Virol., 37:1028–1043; Varmus et al., 1981, Cell, 25:23–26; Varmus et al., 1981, Virology, 108:28–46; Mathey-Prevot et al., 1984, J. Virol., 50:325–334; and Ryan et al., 1985, *Mol. Cell. Biol.,* 5:3477–3582). Preferably, the infected cells are exposed to the cytotoxic or chemotherapeutic agents under conditions where cells that have reverted to a non-transformed phenotype are contact inhibited, and are less susceptible to cytotoxic agents present in the culture medium. This further contributes to the preferential elimination of rapidly growing or transformed cells and, after several cycles, the eventual isolation of cells that have partially or fully reverted to the noncancerous or non-transformed phenotype. The "activated" genes responsible for correcting the transformed phenotype, or suppressing the tumorigenic phenotype, can subsequently be rapidly identified by DNA sequencing using the described 3' RACE protocols.

The presently described methods are also useful for identifying the genetic basis of cancer. Cancers that may be studied, and potentially corrected, using the presently described methods include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor, chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiforme, oligodendroglioma, schwannoma, retinoblastoma, congenital tumors), spinal cord (neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, endometrioid tumors, celioblastoma, clear cell carcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma [embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles, dysplastic nevi, lipoma, angioma, dermatofibroma, keloids, psoriasis; Breast: carcinoma and sarcoma, and Adrenal glands: neuroblastoma.

Modifications to the above studies include the use of retroviral gene trapping vectors in conjunction with a chimeric integrase that targets, or biases, retroviral integration to genes regulated by specific control sequences or transcription factors. For example, the presently described retroviral gene activation vectors can be packaged into a virus incorporating a p53-chimeric integrase (as described in U.S. applic. Ser. No. 08/907,598, now U.S. Pat. No. 6,139,833,) that preferentially targets vector-mediated gene activation to genes regulated by this known tumor suppressor activity.

Appropriately modified, the presently described vectors additionally provide a vehicle for placing virtually any DNA sequence throughout the target cell genome and rapidly identifying where the vectors have integrated. A growing number of DNA sequences have been identified that one might wish to place throughout the genome. Examples of such sequences include recombination sites such as frt sites or lox P sites respectively identified by flp and cre recombinases. Although these sites can be placed throughout the genome by homologous recombination or other transformation methods, the present invention allows for the rapid identification and cataloging of the integration sites using automated processes. These recombination sites can be used for specific DNA insertion or, along with insertions in other positions, and they can be used to create chromosomal rearrangements such as inversions, deletions and translocations. Thus the presently described vectors are particularly useful for studying gene function through chromosomal rearrangements. Other sequences one might wish to place throughout the genome include, but are not limited to, tet, ecdysone, or estrogen receptor DNA binding sites or response elements. These sites are commonly used for inducing or repressing gene expression and by placing these sites throughout the genome, preferably in tens of thousands of different genes, will provide an opportunity to create conditional or tissue-specific regulation of gene expression.

An additional feature of the described mutagenesis strategy is that vector encoded sequences and structural features can be exploited to allow the rapid identification of genomic DNA directly flanking the integrated gene trap constructs. This approach exploits the fact that exon sequence identifying the gene into which the construct has integrated is accessible via the sequence acquisition capabilities of the 3' gene trap cassette. Oligonucleotides that hybridize to suitably identified (by bioinformatics) cellular exons can be used in conjunction with oligonucleotides that hybridize to vector encoded sequence in PCR reactions that produce templates that can be cloned, or directly sequenced to identify the integration site. Where PCR might not prove wholly suitable, PCR reactions can be augmented by using vectors that have been engineered to incorporate a relatively rare cutter restriction site, e.g., Sfi I, etc. Such restriction sites can be exploited to subclone the PCR products, or even genomic sequence flanking the vector, into suitable cloning vectors, or libraries thereof, that can subsequently be used to, for example, identify vector integration sites using established methods, e.g., PCR, long-range PCR, cycle sequencing, etc.

Another aspect of the present invention places a gene encoding a recombinase activity (e.g., flp or cre, etc., see U.S. Pat. Nos. 5,654,182 and 4,959,317 herein incorporated by reference) into the vector containing the described 3' gene trap cassette. The recombinase gene can be expressed in a manner similar to that described for the marker genes, supra. In brief, the recombinase can be expressed from an independent expression cassette, can be incorporated into a 5' gene trap, or can be expressed from a vector promoter. Depending on the strategy employed to express the recombinase, it can be present on a separate construct, or in the vector either 5' or 3' from the 3' gene trap cassette. By incorporating the recombinase gene into the described gene trap vectors, a collection, or library, of mutated cells can be obtained that express the recombinase in essentially the same pattern as the various trapped genes. The above discussion describes just a few examples of how the presently described vectors can be used to place any DNA sequence throughout the genome in a manner that allows for the rapid identification of where the vectors have integrated into the target cell genome. Those skilled in the art will appreciate that the described vectors constitute technology of broad applicability to the field of eukaryotic molecular genetics. As such any of a wide variety of vectors and genetic applications are contemplated as within the scope of the present disclosure. For example, retroviral vectors can be designed that contain a 3' gene trap cassette without the other described features, or downstream from a mutagenic mini-exon and/or a transcription terminator and/or a self-cleaving RNA sequence. Additionally, 3' gene traps can be designed with tandem promoters where the one of the promoters is inducible. Alternatively, hybrid gene traps are also contemplated where, for example, the SAneo from the described 5' gene trap had been fused, preferably in-frame, to the exon of the described 3' gene trap cassette (i.e., deleting the pA and promoter sequences). Such a construct takes advantage both the enhanced SA and SD functions of the described gene trap cassettes, and allows for the automated identification of the genes expressed in a given,target cell. Optionally, such a construct is used in conjunction with an upstream mutagenic mini-exon.

5.5.3. Conditional Mutagenesis

Another aspect of the present invention is the ability to produce mutations that can be switched on and off temporally and spatially in cells or in an organism or animal. The ability to mutate a gene only in a specific place or at a specific time has important implications for understanding gene function. For example, the orientation of SAβgeo within an intron regulates its ability to trap, and thus mutate, the normal transcript produced by the trapped gene. Suitably oriented frt recombinase sites can be used in conjunction with flp recombinase to effect the above genome rearrangements (i.e., "flip", or even remove, the gene trap cassette and thus turn the mutation "on" or "off"). Alternatively, the cre/lox system, for example, can also be employed to produce conditional mutations where a given mutagenic construct can be selectively modified (replaced, flipped, deleted, etc.) only in tissues or cells expressing the cre recombinase.

To validate the above concept, a vector was constructed that placed the SAβgeo cassette within two inverted lox sites. These sites are recognized by the cre recombinase which can effectively flip DNA sequences located in between the lox sites. A retroviral vector containing SAβgeo flanked by inverted lox sites was integrated into an intron of the HPRT gene by homologous recombination. When SAβgeo was present in the forward orientation, HPRT function was abolished as demonstrated by survival of cells in the presence of 6-thioguanine. However, when cre recombinase was expressed in these cells, the orientation of SAβgeo was flipped to the reverse orientation and HPRT function was regained as demonstrated by growth of cells in HAT containing medium. Thus, the HPRT gene was effectively switched off or on by flipping the orientation of SAβgeo. Accordingly, an additional embodiment of the present invention is drawn to vectors that enable the selective and reversible modulation of gene expression. Using a similar methodology, gene trap mutations can also be made conditional or tissue-specific by linking recombinase expression, and hence the flipping of SAβgeo, for example, to various stimuli/control elements. It is also possible to engineer an allelic series using a recombinase-mediated strategy to "swap" in or out, i.e., or engineer, any of a variety of more or less mutagenic constructs (appropriately flanked by lox or frt sites).

An alternative strategy for using the presently described vectors for tissue-specific or regulatable expression is to place specific DNA binding sites such as frt or lox sites within the LTRs. With lox sites in the LTRs, once an insertion is made and identified, the cre recombinase, for example, can be added and used to remove the entire insert except for one LTR containing a single frt or lox site. Additionally, a DNA response element that allows regulatable gene expression can be incorporated, wholly or in part, in conjunction with the recombinase sites. When the vector or gene trap insert is removed by the recombinase activity, the same recombination event that results in the production of the single LTR will also produce a functional DNA response element. This single LTR does not interfere with gene function, but the DNA element can be used to modulate gene expression. Typical DNA elements or operators used for modulating eukaryotic gene expression include the tet, ecdysone or estrogen DNA binding sites. The presence of the tet operator in combination with the tet repressor protein would allow the expression of the gene to be modulated up and down. This can be carried out in mice by breeding the line of mice carrying the LTR insertion with lines of mice expressing the tet repressor either ubiquitously or only in specific tissues.

Another embodiment of the present invention is based on the fact that the flp recombinase, for example, can mediate the replacement of frt flanked integrated vector sequences with exogenously added frt flanked sequences. Accordingly, once a suitably constructed vector (incorporating flanking recombinase sites) is incorporated into a given region of the target cell genome, virtually any of a wide variety of DNA sequences (i.e., promoters, enhancers, IRES, response elements, etc.) that also incorporate the same flanking recombinase sites can be exchanged into or out of the vector by employing the proper recombinase protein.

5.5.4. Biological Assays

As is evident, vectors, particularly retroviral vectors, incorporating the presently described 3' gene trap cassette can be used to mutagenize, activate, or control the expression of endogenous genes in a wide variety of eukaryotic target cells. Accordingly, the presently described vectors are particularly useful to practice molecular genetic techniques in plants a swell as higher eukaryotes such as birds, fish, and mammals. Examples of such molecular genetic techniques include both in vitro and in vivo screens for gene activation, mutation, and regulation.

For example, CD4 positive human T cells can be infected with the presently described vectors in vitro, and subsequently infected with a cytopathic strain of human immunodeficiency virus (HIV). Cells that are capable of surviving HIV infection, can be isolated and rapidly screened for genetic mutations that are associated with HIV resistance.

Another screening strategy that can be employed in vitro is mutating transformed cells with the described gene trap vectors and selecting for mutations that prevent rapid proliferation of the transformed cells. This strategy can be used to identify oncogenes or tumor suppressor genes. After mutation of the cells, various chemicals can be used to kill cells that divide rapidly in order to select for insertions in genes that play a role in cell proliferation and the transformed phenotype. One example of a chemical that kills rapidly proliferating cells is bromodeoxyuridine (BrdU), Pestov and Lau, 1994, Proc. Natl. Acad. Sci., USA, 91(26):12549–12553. BrdU preferentially intercalates into the DNA of rapidly dividing cells and, after the addition of Hoechst 33258, treatment with fluorescent light negatively selects against rapidly dividing cells while simultaneously selecting for slow growing cells.

Another application of cells transduced with the described vectors is cell based in vitro phenotypic screens that can be conducted using heterozygous cells, or using cells that have been cultured or manipulated to homozygosity (using, for example, high concentrations of antibiotics to select for homozygous representation of the corresponding selectable marker gene incorporated into an applicable gene trap vector) prior to such screening assays.

An in vivo assay contemplated by the present invention includes the application of vectors employing the 3' gene trap cassette to mutagenize and screen animals in vivo. In these assays, the present vectors are used in place of, or in addition to classical chemical mutagens such as, for example, ENU (see generally, Vitaterna et al., 1994, Science, 264:719–725). For example, test animals can be infected in various locations, and with varying concentrations of the presently described viral vectors. Preferable modes of administration include oral, intranasal, rectal, topical, intraperitoneal, intravenous, intramuscular, subcutaneous, subdermal, intracranial, intrathecal, and the like. The aberrant cellular phenotypes resulting from such mutagenic stimuli can then be identified, isolated, and screened. Where tumor cells are observed and isolated, 3' RACE can be used to rapidly identify the mutation associated with the tumorigenic phenotype, and thus identify a candidate tumor suppressor gene or potential oncogene.

An additional in vivo application of the presently described vectors involves the generation of mutant transgenic, and somatic transgenic, cells, animals, and plants that are abnormally resistant or susceptible to infection by pathogens associated with infectious diseases.

Another powerful application of the present invention is the large scale production of mutant nonhuman transgenic animals. Such nonhuman transgenic animals may include, for example, transgenic pigs, transgenic rats, transgenic rabbits, transgenic cattle, transgenic goats, and other transgenic animal species such as birds and fish, particularly mammalian species, known in the art. Additionally, bovine, ovine, and porcine species, other members of the rodent family, e.g., rat, as well as rabbit and guinea pig and non-human primates, such as chimpanzee, may be used to practice the present invention. Particularly preferred animals are rats, rabbits, guinea pigs, and most preferably mice. Both somatic cell transgenic animals (see above), and germ line transgenic animals are specifically contemplated. Additionally, such animals are a source of tissues and cells for further gene trapping studies using cultured cells.

The production of mutations in mouse embryonic stem cells by homologous recombination is well established and has proven useful for studying gene function in a mammalian system. However, homologous gene targeting suffers from a number of limitations. One such limitation is the need for a gene to be both known and mapped in order to determine exon/intron structure of the genomic sequence. Even when a gene and its structure are known, a targeting vector must be made for each individual gene one wishes to mutate. This limits the speed at which large numbers of genes can be mutated by homologous recombination. The presently described methods of non-homologous, or nonspecific, 3' gene trapping and mutation do not suffer from the above limitations. Generally, nonspecifically inserted, or nontargeted, vectors can be distinguished from vectors designed for homologous recombination by the fact that such vectors lack the (often extensive) flanking regions of homologous targeting sequence typical of DNA vectors designed to insert sequence by homologous recombination (see, for example, U.S. Pat. No. 5,733,761 herein incorporated by reference).

Other methods can be used to create mutations in mice. These include chemical or radiation induced mutations which can be used to mutate genes without any prior knowledge of the gene. These mutations can be made on a large scale but often require lengthy and involved processes to identify the mutated genes by, for example, positional cloning. Additionally, these mutations are identified only after large numbers of mice are screened for phenotypes. This necessitates a large mouse colony, the great expense of maintaining this colony, and time for breeding animals. Methods are required that allow the rapid mutation of genes regardless of prior knowledge of the gene and allow the gene to be easily identified. Gene trapping as described in the present invention confers the ability to mutate large numbers of genes and to allow the (almost) simultaneous identification of the mutations while still in the embryonic stem cell stage. This allows for substantial analysis before without incurring the costs of large scale mouse production, and, as discussed supra, provides a powerful gene discovery component. Mice can subsequently be produced from ES cells containing gene trap mutations in the genes selected, and the resulting phenotypes can be rapidly identified and characterized. The resulting knockout mice can subsequently be bred with other mouse strains, and, back crossed to produce congenic or recombinant congenic animals that allow for the evaluation of the gene trap mutation in different genetic backgrounds. A representative listing of various strains and genetic manipulations that can be used to practice the above aspects of the present invention (including the ES cell libraries) is provided in "Genetic Variants and Strains of the Laboratory Mouse" 3rd Ed., Vols. 1 and 2, 1996, Lyon et al., eds., Oxford University Press, NY, N.Y., herein incorporated by reference in its entirety.

Given that altered cellular phenotypes can be associated with the presently described methods of gene trapping and activation, additional aspects of the invention are the use of screening assays to detect altered cellular and animal phenotypes. Altered phenotypes can also be detected upon exposing the mutated cells and animals to exogenous materials and compounds. Additionally, the genes/proteins associated with the mutant phenotypes can be isolated and subject to further biochemical analysis to identify drug candidates that can alter, replace, interact with, inhibit, or augment the normal function of the protein.

The present invention is further illustrated by the following examples, which are not intended to be limiting in any way whatsoever.

6.0. EXAMPLES

When vectors containing both SAβgeo (as a 5' exon trap) and PGKpuroSD (as a 3' exon trap) were tested, it was found that 13 times as many G418 resistant colonies were obtained as compared to puro resistant colonies. This indicated that, in many cases, when SAβgeo trapped a gene, the puro SD portion of the gene trap vector was unable to effectively trap the 3' portions of the same gene (as evidenced by the failure to confer puromycin resistance to the target cell). In addition, when the: G418 resistant colonies were isolated and subjected to 3' RACE to determine whether puro was splicing into downstream exons but not at sufficiently high levels to provide puro selection, it was found that only about 10% of the colonies yielded a 3' RACE product. Moreover, the sequence data indicated that splicing was not occurring in the majority of cases. These data indicated that the PGKpuroSD 3' gene trap cassette could only splice into and trap downstream exons of genes with limited efficiency. Similar inefficiencies have also been observed using a variety of other selectable markers in addition to puro. This could be due to the fact that most selectable markers are derived from microorganisms. For example, the puro gene was derived from *Streptomyces alboniger* and therefore incorporates a codon usage that is distinct from that typically used by mammalian cells.

In order to test whether codon usage was responsible for the observed inefficiency in splicing, a puro gene was synthesized that incorporated an optimal mammalian codon usage. However, 3' gene trap cassettes that incorporated the modified puro exon were not efficiently spliced. Another possible reason for inadequate splicing is that the puromycin marker is 700 bp long whereas the average length of a first exon is only about 100 bp. Thus, it further remained possible that placing a selectable marker gene next to a promoter hindered the optimal recognition of the puro exon and splice donor sequence by the splicing machinery.

Given the important discovery that the cellular RNA splicing machinery could only process the puro gene exon with limited efficiency, it was reasoned that 3' gene trap cassettes incorporating naturally occurring mammalian exons might exhibit markedly enhanced splicing, and hence trapping, efficiencies. To test this hypothesis, a 3' gene trap cassette was engineered that replaced the puro exon and splice donor site with a naturally occurring mouse exon with a native splice donor sequence as well as a portion of the naturally occurring intronic sequence following the splice donor site (the first exon of the mouse btk gene, nucleotides 40,043 to 40,250 of GenBank accession number MMU58105). This cassette was subsequently inserted 3' to the SAβgeo gene in a viral gene trap vector. The first exon of the mouse btk gene was selected because it is about the size of an average mammalian first exon and, importantly, it had previously been determined that, although it naturally occurs in the murine genome, the btk gene is not expressed in murine ES cells. This feature is important because if it were expressed in ES cells, the 3' RACE product would always be contaminated with btk sequence from the endogenous gene and might hinder the ability to identify the trapped genes. Consequently, a preferred feature of the 3' gene trap cassette exon is that it is derived from a naturally occurring gene that is not normally expressed by the target cell, or not expressed absent external stimulus or manipulation.

Exons that can be incorporated into the presently described 3' gene trap cassette can be taken or derived from sequences that naturally occur in any of a wide variety of eukaryotic cells (e.g., yeast, insect, fungi, plants, birds, reptiles, fish, etc.), although animal cells, specifically mammalian cells, are typically preferred. Alternatively, exons can be designed and synthesized (e.g., "consensus" exons) such that they can be efficiently and functionally processed by the mRNA processing machinery of the eukaryotic target cell (e.g., splicing, capping, polyadenylation, transport, and degradation).

Although the first exon of btk has been specifically exemplified herein, the present invention is not limited to this exon. Virtually any naturally occurring exon of an eukaryotic gene, series of exons from one or more eukaryotic genes, consensus exon, or synthetic exon or exons that are readily recognized and efficiently processed by the target cell RNA processing and expression machinery can be incorporated into the presently described 3' gene trap cassette. Typically, the first exons are less than about 1,000 bp in length, more preferably less than about 700 bp, and more preferably less than about 500 bp, and most preferably less than about 300 bp in length. Examples of such first exons can be found in, for example, GenBank, and include, but are not limited to, the first exons from human growth hormone, erythropoietin, hprt, metallothionein I and II, maize, wheat, or soybean ribulose 1,5-bisphosphate carboxylate, rat preproinsulin, male sterility 2 (MS2) gene, prolifera (PRL) gene, etc.

Given that typical antibiotic resistance markers are not native to animal or mammalian cells, markers that confer antibiotic resistance or sensitivity (Herpes thymidine kinase) to mammalian target cells are generally not preferred for incorporation into the presently described 3' gene trap cassettes. Similarly, given that typically available enzymatic markers that might be used in chromogenic assays for the detection and selection of gene trap events (such as β-galactosidase, horse radish peroxidase, bacterial alkaline phosphatase, etc.) are also not native to the mammalian genome, such genes are not preferred for the practice of the present invention. However, if suitable genetic manipulations were found that increase the efficiency with which transcripts encoding the above selectable and enzymatic markers are processed and expressed by mammalian cells, such markers could be used to practice the claimed invention. Although the above selectable markers and enzymatic reporters are preferably not part of the presently described 3' gene trap cassette, they can be used as part of the 5' gene trap component in combination with the described 3' gene trap cassette.

6.1. Vector Construction

The promoter from the mouse phosphoglycerate kinase (PGK) gene was placed upstream from the first exon of the naturally occurring murine btk gene (nucleotides 40,043 to 40,250 of the murine btk gene). The first exon of the btk gene does not contain a translational start site and initiation codon marking the 5' region of the coding sequence; however, these features could be engineered into the exon if desired. The 3' end of the coding region of the first exon is marked by a splice donor sequence. Given that splice donor recognition sequences can extend into intronic sequence, 103 bases of intron DNA was retained after the end of the btk first exon. The PGKbtkSD cassette lacks a 3' polyadenylation signal. Accordingly, any transcript produced by the cassette cannot be properly processed, and therefore identified by 3' RACE, unless the transcript is spliced to a 3' exon that can be polyadenylated.

The above 3' gene trap cassette was placed into a retroviral vector (in reverse orientation relative to the flanking LTR regions) that incorporated a polyadenylation site 5' to the PGK promoter of the 3' gene trap cassette, the neo gene was placed 5' to the polyadenylation site, and a splice acceptor (SA) site was placed 5' to the neo coding region to produce a functional SAneopA, or optionally a SAIRESneopA 5' gene trap cassette. This vector also incorporates, in operable combination, a pair of recombinase recognition sites that flank the PGKbtkSD cassette (See FIG. 2). This vector typically requires that the target cell naturally express the trapped gene; however, this requirement can be overcome by adding a promoter that independently controls the expression of the selectable marker. FIG. 2 additionally indicates the preferred locations of optional features such as the mutagenic mini-exon and one or more mutagenesis enhancer regions.

6.2. 3' Gene Trapping

The btk vector was introduced into the embryonic stem cells using standard techniques. In brief, supernatant from GP+E packaging cells was added to approximately $2 \times 10^6$ embryonic stem cells (at an input ratio of approximately 0.1 virus/target cell) for 16 hours and the cells were subsequently selected with G418 for 10 days. G418 resistant cells were subsequently isolated, grown up on 96-well plates and subjected to automated RNA isolation, reverse transcription, PCR and sequencing protocols to obtain the gene trapped sequences.

RNA Isolation was carried out on DNA bind plates (Coming/Costar) treated with 5'-amino $(dT)_{42}$ (GenoSys Biotechnologies) in 50 mM Sodium Phosphate buffer, pH 8.6, and allowed to sit at room temperature overnight. Immediately prior to use the plates were rinsed three times with PBS and twice with TE. Cells were rinsed with PBS, lysed with a solution containing 100 mM Tris-HCl, 500 mM LiCl, 10 mM EDTA, 1% LiDS, and 5 mM DTT in DEPC water, and transferred to the DNA binding plate where the mRNA was captured. After a 15 minute incubation the RNA was washed twice with a solution containing 10 mM Tris-HCl, 150 mM LiCl, 1 mM EDTA, and 0.1% LiDS in DEPC water. The RNA was then rinsed three times with the same solution minus LiDS. Elution buffer containing 2 mM EDTA in DEPC water was added and the plate was heated at 70° C. for five minutes. An RT premix containing 2×First Strand buffer, 100 mM Tris-HCl, pH 8.3, 150 mM KCl, 6 mM $MgCl_2$, 2 mM dNTPs, RNAGuard (1.5 units/reaction, Pharmacia), 20 mM DTT, QT Primer (3 pmol/rxn, GenoSys Biotechnologies, sequence: 5' CCAGTGAGCAGAGT-GACGAGGACTCGAGCT-CAAGCTTTTTTTTTTTTTTTTT 3', (SEQ ID NO: 17) and Superscript II enzyme (200 units/rxn, Life Technologies) was added. The plate was transferred to a thermal cycler for the RT reaction (37° C. for 5 min. 42° C. for 30 min. and 55° C. for 10 min).

6.2.1. PCR Product Generation

The cDNA was amplified using two rounds of PCR. The PCR premix contains: 1.1×MGBII buffer (74 mM Tris pH8.8, 18.3 mM Ammonium Sulfate, 7.4 mM $MgCl_2$, 5.5 mM 2ME, 0.11% Gelatin), 11.1% DMSO (Sigma), 1.67 mM dNTPS, Taq (5 units/rxn), water and primers. The sequences of the first round primers are: $P_0$ 5' AAGCCCGGTGCCTGACTAGCTAG3', SEQ ID NO: 18; $BTK_0$ 5' GAATATGTCTCCAGGTCCAGAG3', SEQ ID NO: 19; and $Q_0$ 5' CCAGTGAGCAGAGTGACGAGGAC3', SEQ ID NO: 20 (pmol/rxn). The sequences of the second round primers are $P_i$ 5' CTAGCTAGGGAGCTCGTC3', SEQ ID NO: 21; $BTK_1$ 5' CCAGAGTCTTCAGAGATCAAGTC3', SEQ ID NO: 22; and $Q_1$ 5' GAGGACTCGAGCTCAAGC3', SEQ ID NO: 23 (50 pmol/rxn). The outer premix was added to an aliquot of cDNA and run for 17 cycles (95° C. for 1 min. 94° C. for 30 sec., 58° C. for 30 sec 65° C. for 3.5 min). An aliquot of this product was added to the inner premix and cycled at the same temperatures 40 times.

The nested 3' RACE products were purified in a 96-well microtiter plate format using a two-step protocol as follows. Twenty-five microliters of each PCR product was applied to a 0.25 ml bed of Sephacryl® S-300 (Pharmacia Biotech AB, Uppsala, Sweden) that was previously equilibrated with STE buffer (150 mM NaCl, 10 MM Tris-HCl, 1 mM EDTA, pH 8.0). The products were recovered by centrifugation at 1200×g for 5 minutes. This step removes unincorporated nucleotides, oligonucleotides, and primer-dimers. Next, the products were applied to a 0.25 ml bed of Sephadex® G-50 (DNA Grade, Pharmacia Biotech AB) that was equilibrated in MilliQ $H_2O$, and recovered by centrifugation as described earlier. Purified PCR products were quantified by fluorescence using PicoGreen (Molecular Probes, Inc., Eugene Oreg.) as per the manufacturer's instructions.

Dye terminator cycle sequencing reaction with AmpliTaq® FS DNA polymerase (Perkin Elmer Applied Biosystems, Foster City, Calif.) were carried out using 7 pmoles of primer (Oligonucleotide OBS; 5' CTGTAAAACGACGGCCAGTC3', SEQ ID NO: 24) and approximately 30–120 ng of 3' RACE product. The cycling profile was 35 cycles of 95° C. for 10 sec, 55° C. for 30 sec, and 60° C. for 2 min. Unincorporated dye terminators were removed from the completed sequencing reactions using G-50 columns as described earlier. The reactions were dried under vacuum, resuspending in loading buffer, and electrophoresed through a 6% Long Ranger acrylamide gel (FMC BioProducts, Rockland, Me.) on an ABI Prism® 377 with XL upgrade as per the manufacturer's instructions.

The automated 96-well format was used to obtain sequence, and data was obtained from 70% of the colonies. Upon examination, the sequence from the first exon of btk was identified followed by the btk splice junction. The splice junction was followed by unique sequences from each separate gene trap event. These sequences averaged 500 bp in length and were of high quality often containing long open reading frames. In addition 80% of these sequences can be matched using blast searches to sequences found in the GenBank database indicating that transcribed exonic sequences were identified. These gene trap sequence tags are of significantly better length and quality than those produced by previous gene trap designs. The new tags are improved in both length and quality and the fact that 80% of the tags match GenBank sequences suggests that they efficiently trap genes.

These data indicate that the splicing machinery is better able to recognize an exon type sequence present adjacent to or relatively close to a promoter when splicing into downstream exons. These data also indicate that the majority of G418 resistant colonies can be identified using gene trap sequence tags. DNA sequence data had already been obtained that represents approximately 7,000 different genes trapped by a vector incorporating a PGKpuroSD 3' gene trap cassette in conjunction with puro selection. Given that it has already been established that such vectors typically produce 13 fold more G418 resistant colonies than puro colonies, vectors incorporating the presently described 3' gene trap cassette have a very large target size, probably well over 70,000 genes. This target can be further increased by using SAneopA rather than the SAβgeo fusion to increase the sensitivity of antibiotic selection, and any other selectable, or otherwise identifiable, marker could be used in the 5' gene trap cassette instead of neo. The use of IRESneo increased the number of G418 resistant colonies to over 15×the number of puro resistant colonies demonstrating its increased sensitivity. Other potential 5' trapping markers include, but are not limited to, antibiotic resistance genes (e.g., β-lactamase), calorimetric marker genes, genes encoding recombinase activity (e.g., flp or cre, etc.), enzymes, fluorescent marker genes (e.g., genes encoding activities that directly or indirectly mediate cellular fluorescence) such as the gene encoding green fluorescent protein, and assays for detecting the same, which are described, inter alia, in U.S. Pat. No. 5,625,048, herein incorporated by reference.

Typically, the more sensitive the selectable marker, the greater the number of target genes that can be trapped. The ability to use the btk first exon to obtain gene trap sequence tags from the 3' exons of the G418 resistant colonies produced approximately 13 fold more mutated cells than could be mutated and rapidly sequenced using previous vectors, and thus represents a significant improvement in gene trapping technology.

Given the above results, it is clear that the surprising and unexpected properties that resulted in an order of magnitude improvement over any previously reported 3' gene trap cassettes were only realized by departing from our established selectable marker paradigm for gene trapping.

6.3. Pharmacogenomics

As discussed above, an additional method of augmenting the target size of the described vectors and constructs is to dispense with selection all together, and use other, i.e., molecular genetic, means to isolate trapped exons. Using such an approach allows for the rapid generation and analysis of gene sequence information. In addition to providing a clear advantage with respect to the speed of sequence acquisition, the sequencing of gene trapped libraries allows for substantial cost savings because of the reduced rate of repeat sequences relative to conventional cDNA libraries. The economies inherent in the presently described system of sequence acquisition make it practical to rapidly obtain a broad based survey of an individual's genome, or a collection of individuals' genomes, to identify, inter alia, genetic polymorphisms, particularly SNPs and cSNPs, that can be associated with the disease (where a portion of the individuals surveyed are known to manifest common disease traits or symptoms). Additionally, similar methods can be employed in broad-based genomic assays that identify the genetic basis for behavioral traits, drug susceptibility, drug sensitivity, drug allergy, etc. in both humans and nonhuman animals.

In such methods, high-to-saturating concentrations of constructs comprising the described 3' gene trap cassette can be introduced into suitable target cells, including primary human or non-human cells (for example, primary nucleated blood cells such as leukocytes and lymphocytes, etc.), using established methods. After the 3' sequence acquisition cassette has integrated into the target cell genome, RNA is isolated from the target cells, cDNA is produced (and optionally PCR amplified as described above), and a cDNA library is constructed. The library is subsequently sequenced and catalogued/compared relative to a control library as well as other "experimental", libraries. As SNPs, cSNPs, or other more gross polymorphisms are identified that correlate with the "experimental" or "disease" groups, a catalog of genetic polymorphisms will be developed that provides both a multi-loci analysis as well as highlights the regions of the genome that correlate with specific diseases, or may other wise warrant further study and analysis. Such information can also prove valuable for the identification of genetic polymorphisms associated with drug effectiveness (or adverse drug reactions), as well as the design of diagnostic assays.

7.0. Reference to Microorganism Deposits

The following plasmid has been deposited at the American Type Culture Collection (ATCC), Manassas, Va., USA, under the terms of the Budapest Treaty on the International Recognition of the Deposit of Microorganisms for the Purposes of Patent Procedure and Regulations thereunder (Budapest Treaty) and is thus maintained and made available according to the terms of the Budapest Treaty. Availability of such plasmid is not to be construed as a license to practice the invention in contravention of the rights granted under the authority of any government in accordance with its patent laws.

The deposited plasmid has been assigned the indicated ATCC deposit number:

Plasmid ATCC No.

pbtK 209712

All publications and patents mentioned in the above specification are herein incorporated by reference. Various modifications and variations of the described invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of animal genetics and molecular biology or related fields are intended to be within the scope of the following claims.

What is claimed is:

1. A vector comprising:
   a) a 5' gene trap cassette, comprising in operable combination:
      1) a splice acceptor;
      2) a first exon sequence located 3' to said splice acceptor, said first exon encoding a marker enabling the identification of a cell expressing said exon; and
      3) a polyadenylation sequence defining the 3' end of said first exon; and
   b) a 3' gene trap cassette located 3' to said polyadenylation sequence comprising in operable combination:
      1) a first promoter;
      2) a second exon sequence located 3' from and expressed by said promoter, said second exon not encoding an activity conferring antibiotic resistance; and
      3) a splice donor sequence defining the 3' region of the exon; and
   wherein said vector does not encode a promoter mediating the expression of said first exon, and wherein said vector does not encode a sequence that mediates the polyadenylation of an mRNA transcript encoded by said second exon sequence and expressed by said first promoter.

2. A vector according to claim 1 wherein said first exon additionally encodes an internal ribosome entry site operatively positioned between said splice acceptor and an initiation codon of said first exon.

3. The vector of claim 1 wherein said second exon and splice donor sequences are the same as or substantially the same as sequences existing in a naturally occurring eukaryotic gene.

4. The vector of claim 1 additionally incorporating in the region between said polyadenylation sequence and said promoter at least one mutagenesis enhancer selected from the group consisting of a transcription termination sequence, a 3' terminal exon, and a sequence encoding a self-cleaving RNA.

5. The vector of claim 1 wherein said first exon encodes a marker selected from the group consisting of a marker conferring antibiotic resistance, a marker conferring antibiotic sensitivity, an enzymatic marker, a cre recombinase, a flp recombinase, and a fluorescently detectable marker.

6. The vector of claim 5 wherein said marker encodes neomycin resistance.

7. A genetically engineered retroviral vector comprising:
   a) a marker gene expressed by a first vector encoded promoter; and
   b) a 3' gene trap cassette comprising in operable combination:
      1) a second vector encoded promoter;
      2) an exon sequence located 3' from and expressed by said second promoter, said exon not encoding an activity conferring antibiotic resistance;
      3) a splice donor sequence defining the 3' region of the exon; and
   wherein said vector does not encode a sequence that mediates the polyadenylation of an mRNA transcript encoded by said exon sequence.

8. A genetically engineered vector comprising:
   a) a 5' gene trap cassette comprising in operable combination:
      1) a splice acceptor;
      2) a first exon sequence located 3' to said splice acceptor, said first exon encoding a marker enabling the identification of a cell expressing said exon; and
      3) a polyadenylation sequence-defining the 3' end of said first exon;
   b) a 3' gene trap cassette located 3' to said polyadenylation sequence and comprising in operable combination:
      1) a promoter;
      2) a second exon sequence located 3' from and expressed by said promoter, said second exon being of non-prokaryotic origin;
      3) a splice donor sequence defining the 3' region of the exon; and
   wherein said vector does not encode a promoter mediating the expression of said first exon, and wherein said vector does not encode a sequence that mediates the polyadenylation of an mRNA transcript encoded by said second exon sequence and expressed by said promoter.

9. An infectious retrovirus comprising a vector according to any one of claims 1, 7 or 8.

10. A method of trapping a gene in a eukaryotic target cell comprising introducing a retrovirus according to claim 9 into said cell in vitro.

11. A method of trapping a gene in a eukaryotic target cell comprising introducing a vector according to any one of claims 1, 7, or 8 into said cell in vitro; wherein said vector is introduced into said target cell by a method selected from the group consisting of electroporation, viral infection, retrotransposition, microinjection and transfection.

12. A eukaryotic cell which has a vector according to any one of claims 1, 7, 8 incorporated into its genome; wherein the vector was introduced into the eukaryotic cell in vitro.

13. A method of activating the expression of a naturally occurring gene in a cell comprising introducing a vector according to any one of claims 1, 7, or 8 into said cell in vitro.

14. The method of claim 13 wherein said cell is a mammalian cell.

15. The method of claim 14 wherein said mammalian cell is selected from the group consisting of a human cell and a mouse cell.

* * * * *